(12) United States Patent
O'Brien et al.

(10) Patent No.: US 7,285,264 B2
(45) Date of Patent: Oct. 23, 2007

(54) PEPTIDE-BASED BODY SURFACE COLORING REAGENTS

(75) Inventors: John P. O'Brien, Oxford, PA (US); Hong Wang, Kennett Square, PA (US); Ying Wu, Wallingford, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/389,948

(22) Filed: Mar. 27, 2006

(65) Prior Publication Data

US 2006/0222609 A1 Oct. 5, 2006

Related U.S. Application Data

(63) Continuation-in-part of application No. 11/074,473, filed on Mar. 8, 2005, which is a continuation-in-part of application No. 10/935,642, filed on Sep. 7, 2004.

(60) Provisional application No. 60/501,498, filed on Sep. 8, 2003.

(51) Int. Cl.
- A61K 8/64 (2006.01)
- A61K 38/02 (2006.01)
- A61Q 5/10 (2006.01)
- C07K 2/00 (2006.01)

(52) U.S. Cl. ............ 424/70.6; 424/70.14; 514/2; 514/14; 514/16; 530/327; 530/329; 530/345

(58) Field of Classification Search ............ None
See application file for complete search history.

(56) References Cited

U.S. PATENT DOCUMENTS

| | | | |
|---|---|---|---|
| 4,416,873 A | 11/1983 | Puchalski et al. | |
| 4,482,537 A | 11/1984 | El-Menshawy et al. | |
| 5,192,332 A | 3/1993 | Lang et al. | |
| 5,223,409 A | 6/1993 | Ladner et al. | |
| 5,403,484 A | 4/1995 | Ladner et al. | |
| 5,425,937 A | 6/1995 | Uchiwa et al. | |
| 5,449,754 A | 9/1995 | Nishioka | |
| 5,480,971 A | 1/1996 | Houghten et al. | |
| 5,490,980 A | 2/1996 | Richardson et al. | |
| 5,571,698 A | 11/1996 | Ladner et al. | |
| 5,585,275 A | 12/1996 | Hudson et al. | |
| 5,597,386 A | 1/1997 | Igarashi et al. | |
| 5,639,603 A | 6/1997 | Dower et al. | |
| 5,801,226 A | 9/1998 | Cummins et al. | |
| 5,837,500 A | 11/1998 | Ladner et al. | |
| 6,013,250 A | 1/2000 | Cannell et al. | |
| 6,232,287 B1 | 5/2001 | Ruoslahti et al. | |
| 6,267,957 B1 | 7/2001 | Green et al. | |
| 6,280,747 B1 | 8/2001 | Philippe et al. | |
| 6,344,443 B1 | 2/2002 | Liu et al. | |
| 6,444,421 B1 * | 9/2002 | Chung .............. | 435/6 |
| 6,537,330 B1 | 3/2003 | Hoeffkes et al. | |
| 6,620,419 B1 | 9/2003 | Lintner | |
| 6,835,868 B1 * | 12/2004 | Misra et al. .......... | 800/301 |
| 2002/0098524 A1 | 7/2002 | Murray et al. | |
| 2003/0152976 A1 | 8/2003 | Janssen et al. | |
| 2003/0185870 A1 | 10/2003 | Grinstaff et al. | |
| 2005/0050656 A1 | 3/2005 | Huang et al. | |
| 2005/0226839 A1 | 10/2005 | Huang et al. | |

FOREIGN PATENT DOCUMENTS

| | | |
|---|---|---|
| EP | 0 453 097 A2 | 10/1991 |
| EP | 0 570 583 A1 | 11/1993 |
| EP | 0 634 161 A1 | 1/1995 |
| JP | 02311412 A | 12/1990 |
| JP | 06065049 A | 3/1994 |
| JP | 08104614 A | 4/1996 |
| JP | 8-143431 A * | 6/1996 |
| JP | 09003100 A | 1/1997 |
| JP | 2002363026 | 12/2002 |
| WO | WO 00/48558 A1 | 8/2000 |
| WO | WO 01/45652 A1 | 6/2001 |
| WO | WO 01/79479 A2 | 10/2001 |
| WO | WO 01/07009 A1 | 2/2002 |
| WO | WO 02/065134 A2 | 8/2002 |
| WO | WO 03/031477 A1 | 4/2003 |
| WO | WO 03/102020 A2 | 12/2003 |
| WO | WO 2004/048399 A2 | 6/2004 |
| WO | WO 2004/069211 A2 | 8/2004 |
| WO | WO 2004/000257 A2 | 12/2004 |

OTHER PUBLICATIONS

Genencor International, Bio Conference, San Francisco, California, Jun. 8, 2004—Meeting Presentation, pp. 1-29.

Cheng-Ting Chien et al., The Two-Hybrid System: A Method to Identify and Clone Genes for Proteins That Interact With a Protein of Interest, Proc. Natl. Acad. Sci., vol. 88:9578-9582, 1991.

David J. Kemp et al., Direct Immunoassay for Detecting *Escherichia coli* Colonies That Contain Polypeptides Encoded by Cloned DNA Segments, Proc. Natl. Acad. Sci., vol. 78(7):4520-4524, 1981.

David M. Helfman et al., Identification of Clones That Encode Chicken Tropomyosin by Direct Immunological Screening of a CDNA Expression Library, Proc. Natl. Acad. Sci., vol. 80:31-35, 1983.

(Continued)

Primary Examiner—Jeffrey Edwin Russel

(57) ABSTRACT

Peptides have been identified that bind with high affinity to body surfaces, such as, hair, skin, nails, teeth, gums, and oral cavity surfaces. Diblock and triblock peptide-based body surface coloring reagents formed by coupling a body surface binding peptide to a pigment binding peptide, either directly or through a spacer, are described. The peptide-based body surface coloring reagents may be used in conjunction with pigments to color body surfaces.

17 Claims, 1 Drawing Sheet

OTHER PUBLICATIONS

Figure 1:
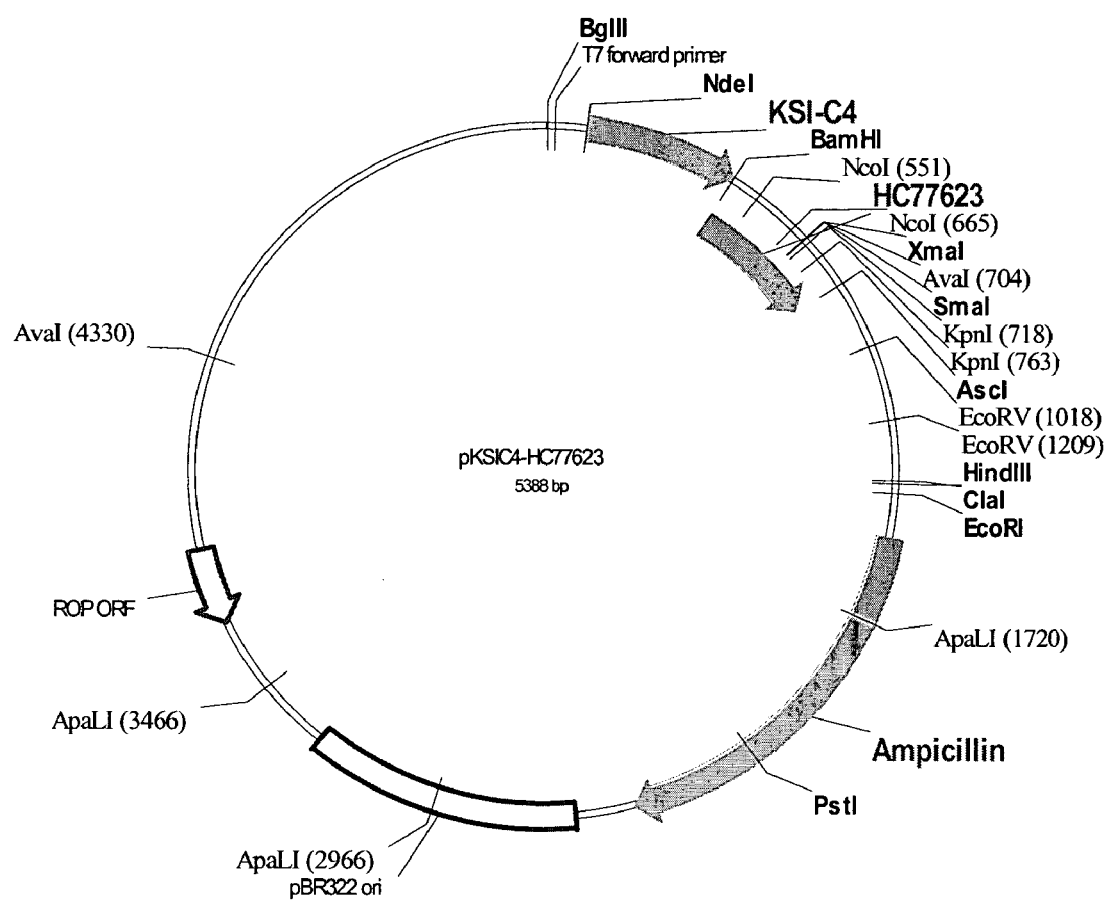

Marc S. Reisch, Ingredients Makers Take Lessons From Biotechnology to Mastermind the Latest in Personal Care, C&EN Northeast News Bureau, pp. 16-21, 2002.

Maria Dani, Biological Libraries, J. of Receptor & Signal Transduction Research, vol. 21(4):447-468, 2001.

Ronald H. Hoess, Protein Design and Phage Display, Chem. Rev., vol. 101:3205-3218, 2001.

S. G. Dixit et al., Combinatorial Chemistry—Principles and Practices, Journal of Scientific & Industrial Research, vol. 57:173-183, 1998.

Todd C. Holmes, Novel Peptide-Based Biomaterial Scaffolds for Tissue Engineering, Trends in Biotechnology, vol. 20(1):16-21-2002.

Sandra R. Whaley et al., Selection of Peptides With Semiconductor Binding Specificity for Directed Nanocrystal Assembly, Nature, vol. 405:665-668, 2000.

* cited by examiner

PEPTIDE-BASED BODY SURFACE COLORING REAGENTS

This patent application is a continuation in part of U.S. patent application Ser. No. 11/074,473, filed Mar. 8, 2005, which is a continuation in part of U.S. patent application Ser. No. 10/935,642, filed Sep. 7, 2004, which claims the benefit of U.S. Provisional Application 60/501,498, filed Sep. 8, 2003.

FIELD OF THE INVENTION

The invention relates to the field of personal care products. More specifically, the invention relates to diblock and triblock peptide-based body surface coloring reagents comprising body surface-binding peptides and pigment-binding peptides that may be used to attach pigments to body surfaces.

BACKGROUND OF THE INVENTION

Colorants for body surfaces, such as hair, skin, and nails are well-known and frequently used in personal care products. Hair coloring agents may be divided into three categories, specifically, permanent, semi-permanent or direct, and temporary. The permanent hair dyes are generally oxidative dyes that provide hair color that lasts about four to six weeks. These oxidative hair dyes consist of two parts, one part contains the oxidative dyes in addition to other ingredients, while the second part contains an oxidizing agent such as hydrogen peroxide. The two components are mixed immediately prior to use. The oxidizing agent oxidizes the dye precursors, which then combine to form large color molecules within the hair shaft. Although the oxidative hair dyes provide long-lasting color, the oxidizing agents they contain cause hair damage. The semi-permanent or direct hair dyes are preformed dye molecules that are applied to the hair and provide color for about six to twelve shampoos. This type of hair dye is gentler to the hair because it does not contain peroxides, but the hair color does not last as long. Some improved durability is achieved by the use of nanoparticle hair coloring materials with a particle size of 10 to 500 nm, as described by Hensen et al. in WO 01045652. These nanoparticle hair coloring materials are conventional direct hair dyes that are treated to obtain nanoscale dimensions and exhibit increased absorption into the hair. Temporary hair dyes are coloring agents that are applied to the hair surface and are removed after one shampoo. It would be desirable to develop a hair coloring agent that provides the durability of the permanent hair dyes without the use of oxidizing agents that damage hair.

The major problem with the current skin colorants, non-oxidative hair dyes, as well as nail coloring agents is that they lack the required durability required for long-lasting effects. For this reason, there have been attempts to enhance the binding of cosmetic agents to the hair, skin or nails. For example, Richardson et al. in U.S. Pat. No. 5,490,980 and Green et al. in U.S. Pat. No. 6,267,957 describe the covalent attachment of cosmetic agents, such as skin conditioners, hair conditioners, coloring agents, sunscreens, and perfumes, to hair, skin, and nails using the enzyme transglutaminase. This enzyme crosslinks an amine moiety on the cosmetic agent to the glutamine residues in skin, hair, and nails. Similarly, Green et al. in WO 0107009 describe the use of the enzyme lysine oxidase to covalently attach cosmetic agents to hair, skin, and nails.

In another approach, cosmetic agents have been covalently attached to proteins or protein hydrolysates. For example, Lang et al. in U.S. Pat. No. 5,192,332 describe temporary coloring compositions that contain an animal or vegetable protein, or hydrolysate thereof, which contain residues of dye molecules grafted onto the protein chain. In those compositions, the protein serves as a conditioning agent and does not enhance the binding of the cosmetic agent to hair, skin, or nails. Horikoshi et al. in JP 08104614 and Igarashi et al. in U.S. Pat. No. 5,597,386 describe hair coloring agents that consist of an anti-keratin antibody covalently attached to a dye or pigment. The antibody binds to the hair, thereby enhancing the binding of the hair coloring agent to the hair. Similarly, Kizawa et al. in JP 09003100 describe an antibody that recognizes the surface layer of hair and its use to treat hair. A hair coloring agent consisting of that anti-hair antibody coupled to colored latex particles is also described. The use of antibodies to enhance the binding of dyes to the hair is effective in increasing the durability of the hair coloring, but these antibodies are difficult and expensive to produce. Terada et al. in JP 2002363026 describe the use of conjugates consisting of single-chain antibodies, preferably anti-keratin, coupled to dyes, ligands, and cosmetic agents for skin and hair care compositions. The single-chain antibodies may be prepared using genetic engineering techniques, but are still difficult and expensive to prepare because of their large size. Findlay in WO 00048558 describes the use of calycin proteins, such as β-lactoglobulin, which contain a binding domain for a cosmetic agent and another binding domain that binds to at least a part of the surface of a hair fiber or skin surface, for conditioners, dyes, and perfumes. Again these proteins are large and difficult and expensive to produce.

Linter in U.S. Pat. No. 6,620,419 describes peptides grafted to a fatty acid chain and their use in cosmetic and dermopharmaceutical applications. The peptides described in that disclosure are chosen because they stimulate the synthesis of collagen; they are not specific binding peptides that enhance the durability of hair and skin conditioners, and hair, nail, and skin colorants.

Peptide-based hair conditioners, hair colorants, and other benefit agents have also been developed to improve the durability of these compositions (Huang et al., copending and commonly owned U.S. Patent Application Publication No. 2005/0050656, and U.S. Patent Application Publication No. 2005/0226839). The peptide-based hair conditioners or colorants are prepared by coupling a specific peptide sequence that has a high binding affinity to hair with a conditioning or coloring agent, respectively. The peptide portion binds to the hair, thereby strongly attaching the conditioning or coloring agent. Peptides with a high binding affinity to hair have been identified using phage display screening techniques (Huang et al., supra; Estell et al. WO 0179479; Murray et al., U.S. Patent Application Publication No. 2002/0098524; Janssen et al., U.S. Patent Application Publication No. 2003/0152976; and Janssen et al., WO 04048399).

Additionally, Reisch (*Chem. Eng. News* 80:16-21 (2002)) reports that a family of peptides designed to target an ingredient of specific human tissue has been developed for personal care applications. However, no description of peptide-based conditioners or coloring agents are disclosed in that publication. Although these peptide-based reagents offer much promise in personal care applications, they generally require covalent coupling of the peptide to the coloring agent. The covalent coupling chemistry may be complex and time consuming, and adds to the cost of the reagent.

In view of the above, a need exists for colorants for body surfaces, such as hair, skin, nails, and teeth that provide improved durability for long lasting effects and are easy and inexpensive to prepare.

Applicants have addressed the stated need by identifying peptide sequences using phage display screening that specifically bind to body surfaces, such as, hair, skin, nails, teeth, gums, and oral cavity surfaces, with high affinity and coupling them with specific pigment-binding peptides to provide diblock and triblock peptide-based reagents that may be used in conjunction with pigments to color body surfaces.

SUMMARY OF THE INVENTION

The invention provides peptide-based body surface coloring reagents comprising a body surface binding peptide and a pigment-binding peptide. These peptide-based reagents may be used in conjunction with pigments to color body surfaces, such as hair, skin, nails, and teeth. The body surface binding peptide binds strongly to the body surface and the pigment-binding peptide binds to the pigment, thereby attaching the pigment to the body surface.

Accordingly, in one embodiment the invention provides a diblock peptide-based body surface coloring having the general structure $[(BSBP)_m\text{-}(PBP)_n]_x$, wherein a) BSBP is a body surface binding peptide;
b) PBP is a pigment-binding peptide; and
c) m, n, and x independently range from 1 to about 10.

In another embodiment, the invention provides a triblock, peptide-based body surface coloring reagent having the general structure $[[(BSBP)_m\text{-}S_q]_x\text{-}[(PBP)_n\text{-}S_r]_z]_y$, wherein a) BSBP is a body surface binding peptide;
b) PBP is a pigment-binding peptide;
c) S is a molecular spacer; and
d) m, n, x and z independently range from 1 to about 10, y is from 1 to about 5, and where q and r are each independently 0 or 1, provided that both r and q may not be 0.

In another embodiment the invention provides aq peptide-based body surface coloring reagent according to the invention wherein the body surface-binding peptide is isolated by a process comprising the steps of:

(i) providing a library of combinatorially generated phage-peptides;
(ii) contacting the library of (i) with a body surface to form a reaction solution comprising:
  (A) phage-peptide-body surface complex;
  (B) unbound body surface, and
  (C) uncomplexed peptides;
(iii) isolating the phage-peptide-body surface complex of (ii);
(iv) eluting the weakly bound peptides from the isolated peptide complex of (iii);
(v) identifying the remaining bound phage-peptides either by using the polymerase chain reaction directly with the phage-peptide-body surface complex remaining after step (iv), or by infecting bacterial host cells directly with the phage-peptide-body surface complex remaining after step (iv), growing the infected cells in a suitable growth medium, and isolating and identifying the phage-peptides from the grown cells.

In another embodiment the invention provides a personal care composition comprising an effective amount of the peptide-based body surface coloring reagent of the invention, comprising a body surface binding peptide and a pigment binding peptide.

In a similar embodiment the invention provides a method for coloring a body surface comprising:

a) providing a pigment;
b) providing a composition comprising a peptide-based body surface coloring reagent according to the invention wherein the body surface binding peptide has affinity for the body surface and the pigment binding peptide has affinity for the pigment; and
c) applying the pigment of (a) with the composition of (b) to a body surface for a time sufficient for the peptide-based body surface coloring reagent to bind to the pigment and the body surface.

Additionally, the invention provides personal care compositions, such as hair coloring, hair conditioning, skin coloring, skin conditioning, cosmetic, oral care, and nail polish compositions, comprising the peptide-based body surface coloring reagents.

BRIEF DESCRIPTION OF FIGURES AND SEQUENCE DESCRIPTIONS

The invention can be more fully understood from the following detailed description, figure and the accompanying sequence descriptions, which form a part of this application.

FIG. 1 is a plasmid map of the vector pKSIC4-HC77623, described in Examples 17-20.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. § 1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1—Sequence Listing" and "Copy 2 Sequence listing" The discs contain the following file: Seq List CL3417 NA.ST25 having the following size: 46,969 bytes and which was created Friday May 19, 2006.

SEQ ID NO:1 is the amino acid sequence of a hair-binding peptide.

SEQ ID NO:2 is the amino acid sequence of a skin-binding peptide.

SEQ ID NOs:3-52, 54-59 are the amino acid sequences of hair-binding peptides.

SEQ ID NO:53 is the amino acid sequence of a hair-binding and nail-binding peptide.

SEQ ID NO:60 is the amino acid sequence of a nail-binding peptide.

SEQ ID NO:61 is the amino acid sequence of a skin-binding peptide.

SEQ ID NO:62 is the oligonucleotide primer used to sequence phage DNA.

SEQ ID NO:63 is the amino acid sequence of a peptide used as a control in the ELISA binding assay, as described in Example 5.

SEQ ID NO:64 is the amino acid sequence of a cysteine-attached hair-binding peptide.

SEQ ID NO:65 is the amino acid sequence of the Caspase 3 cleavage site.

SEQ ID NOs:66, 69, and 70 are the amino acid sequence of shampoo-resistant hair-binding peptides.

SEQ ID NOs:67 and 68 are the nucleotide sequences of the primers used to amplify shampoo-resistant, hair-binding phage peptides, as described in Example 8.

SEQ ID NOs:71-74 are the amino acid sequences of the biotinylated hair-binding and skin-binding peptides used Example 9.

SEQ ID NO:75 is the amino acid sequence of a hair conditioner resistant hair-binding peptide.

SEQ ID NOs:76-98 are the amino acid sequences of hair-binding peptides.

SEQ ID NOs:99-104 are the amino acid sequences of skin-binding peptides.

SEQ ID NOs:105-109 are the amino acid sequences of empirically generated hair and skin-binding peptides.

SEQ ID NOs:110-134 are the amino acid sequences of pigment-binding peptides.

SEQ ID NOs:135-137 are the amino acid sequences of peptide spacers.

SEQ ID NO:138-147 are the amino acid sequences of triblock peptide-based body surface coloring reagents.

SEQ ID NOs:148-151 are the nucleotide sequences that encode the peptide-based body surface coloring reagents given as SEQ ID NOs:144-147.

SEQ ID NO:152 is the nucleotide sequence of plasmid pKSIC4-HCC77623, which is described in Examples 17-20.

SEQ ID NOs:153-156 are the amino acid sequences of hair conditioner and shampoo resistant hair-binding peptides.

DETAILED DESCRIPTION OF THE INVENTION

The present invention provides diblock and triblock peptide-based body surface coloring reagents which comprise at least one body surface-binding peptide coupled to at least one pigment-binding peptide, either directly or through a molecular spacer. These diblock and triblock peptide-based reagents may be used in conjunction with pigments to color body surfaces. Typical of the compositions of the invention are peptide-based hair and skin colorants and nail polish compositions.

The peptide based diblock and triblock peptide-based body surface coloring reagents of the invention provide benefits and an advance over the art in the development of personal care products. Because the reagents are peptide based they are able to bind strongly to body surfaces from an aqueous environment, thus in many cases being both water soluble and water fast. Additionally, because of the aqueous nature of the reagents, they may be removed from body surfaces without of the use of odor producing chemicals. The reagents of the invention bind almost immediately to the target body surface, eliminating the need for long drying times, typical of most personal care applications. Moreover, the peptide-based body surface coloring reagents are used without the need to covalently attach the body surface-binding peptide to the coloring agent. Most importantly, the peptide nature of the reagents makes them virtually non-toxic and non-irritating to exposed body surfaces such as the skin and the membranes of the eyes and mouth.

The following definitions are used herein and should be referred to for interpretation of the claims and the specification.

"HBP" means hair-binding peptide.
"SBP" means skin-binding peptide.
"NBP" means nail-binding peptide.
"OBP" means oral cavity surface-binding peptide.
"TBP" means tooth-binding peptide.
"PBP" means pigment-binding peptide.
"C" means coloring agent for body surfaces such as hair, skin, nails, or teeth.
"S" means spacer.
"BSBP" means body surface binding peptide.

The term "present invention" or "invention" as used herein is meant to apply generally to all embodiments of the invention as recited in the claims as presented, or as later amended and supplemented.

The term "peptide" refers to two or more amino acids joined to each other by peptide bonds or modified peptide bonds.

The term "body surface" refers to any surface of the human body that may serve as a substrate for the binding of a diblock or triblock peptide-based body surface coloring reagent comprising at least one body surface-binding peptide and at least one pigment-binding peptide. Typical body surfaces include but are not limited to hair, skin, nails, teeth, and gums.

The term "hair" as used herein refers to any type of human hair, including eyebrows, eyelashes, and other facial hair.

The term "skin" as used herein refers to human skin, or substitutes for human skin, such as pig skin, Vitro-Skin® and EpiDerm™. Skin as used herein as a body surface will generally comprise a layer of epithelial cells and may additionally comprise a layer of endothelial cells.

The term "nails" as used herein refers to human fingernails and toenails.

The terms "coupling" and "coupled" as used herein refer to any chemical association and includes both covalent and non-covalent interactions.

The term "stringency" as it is applied to the selection of the body-surface-binding peptides, refers to the concentration of the eluting agent (usually detergent) used to elute peptides from the body surface. Higher concentrations of the eluting agent provide more stringent conditions.

The term "peptide-body surface complex" means structure comprising a peptide bound to a sample of a body surface via a binding site on the peptide.

The term "peptide-hair complex" means structure comprising a peptide bound to a hair fiber via a binding site on the peptide.

The term "peptide-skin complex" means structure comprising a peptide bound to the skin via a binding site on the peptide.

The term "peptide-nail complex" means structure comprising a peptide bound to fingernails or toenails via a binding site on the peptide.

The term "peptide-substrate complex" refers to either peptide-hair, peptide-skin, peptide-nail, or peptide teeth complexes.

The term "$MB_{50}$" refers to the concentration of the binding peptide that gives a signal that is 50% of the maximum signal obtained in an ELISA-based binding assay, as described in Example 9. The $MB_{50}$ provides an indication of the strength of the binding interaction or affinity of the components of the complex. The lower the value of $MB_{50}$, the stronger the interaction of the peptide with its corresponding substrate.

The term "binding affinity" refers to the strength of the interaction of a binding peptide with its respective substrate. The binding affinity is defined herein in terms of the $MB_{50}$ value, determined in an ELISA-based binding assay.

The term "nanoparticles" are herein defined as particles with an average particle diameter of between 1 and 200 nm. Preferably, the average particle diameter of the particles is between about 1 and 40 nm. As used herein, "particle size" and "particle diameter" have the same meaning. Nanoparticles include, but are not limited to, metallic, semiconductor, polymer, or silica particles.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or antisense RNA derived from the nucleic acid fragment of the invention. Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

"PCR" or "polymerase chain reaction" is a technique used for the amplification of specific DNA segments (U.S. Pat. Nos. 4,683,195 and 4,800,159).

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides diblock and triblock peptide-based body surface coloring reagents which comprise at least one body surface-binding peptide coupled to at least one pigment-binding peptide, either directly or through a molecular spacer. The body surface-binding peptide sequences and the pigment-binding peptide sequences may be identified using combinatorial methods, such as phage display. Additionally, the body surface-binding peptide sequences may be empirically generated. The diblock and triblock peptide-based reagents of the invention may be prepared by covalently attaching the peptide sequences, either directly or through a molecular spacer. Alternatively, the entire diblock and triblock peptide-based reagents may be produced biologically. The diblock and triblock peptide-based body surface coloring reagents may be used in conjunction with pigments to color body surfaces such as hair, skin, nails, and teeth.

Body Surfaces

Body surfaces of the invention are any surface on the human body that will serve as a substrate for a binding peptide. Typical body surfaces include, but are not limited to hair, skin, nails, teeth, gums, and the tissues of the oral cavity. In many cases the body surfaces of the invention will be exposed to air, however in some instances, the oral cavity for example, the surfaces will be internal. Accordingly body surfaces may include layers of both epithelial and well as endothelial cells.

Samples of body surfaces are available from a variety of sources. For example, human hair samples are available commercially, for example from International Hair Importers and Products (Bellerose, N.Y.), in different colors, such as brown, black, red, and blond, and in various types, such as African-American, Caucasian, and Asian. Additionally, the hair samples may be treated for example using hydrogen peroxide to obtain bleached hair. Human skin samples may be obtained from cadavers or in vitro human skin cultures. Additionally, pig skin, available from butcher shops and supermarkets, Vitro-Skin®, available from IMS Inc. (Milford, Conn.), and EpiDerm™, available from MatTek Corp. (Ashland, Mass.), are good substitutes for human skin. Human fingernails and toenails may be obtained from volunteers. Extracted human teeth and false teeth may be obtained from Dental offices. Additionally, hydroxyapatite, available in many forms for example from Berkeley Advanced Biomaterials, Inc. (San Leandro, Calif.), may be used as a model for human teeth.

Body Surface-Binding Peptides

Body surface-binding peptides as defined herein, are peptide sequences that specifically bind with high affinity to specific body surfaces, including, but not limited to hair, nails, teeth, gums, skin, and the tissues of the oral cavity, for example. Suitable body surface-binding peptide sequences may be selected using combinatorial methods that are well known in the art or may be empirically generated. The body surface binding peptides of the invention have a binding affinity for their respective substrate, as measured by $MB_{50}$ values, of less than or equal to about $10^{-2}$ M, less than or equal to about $10^{-3}$ M, less than or equal to about $10^{-4}$ M, less than or equal to about $10^{-5}$ M, preferably less than or equal to about $10^{-6}$ M, and more preferably less than or equal to about $10^{-7}$ M.

Combinatorially generated body surface-binding peptides of the present invention are from about 7 amino acids to about 50 amino acids, more preferably, from about 7 amino acids to about 25 amino acids in length. The body surface-binding peptides of the present invention may be generated randomly and then selected against a specific body surface, for example, hair, skin, nail, or tooth sample, based upon their binding affinity for the surface of interest. The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci.* USA 80(1):31-35, (1983)), yeast display (Chien et al., *Proc Natl Acad Sci* USA 88(21):9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500). Techniques to generate such biological peptide libraries are described in Dani, M., *J. of Receptor & Signal Transduction Res.*, 21(4):447-468 (2001). Additionally, phage display libraries are available commercially from companies such as New England BioLabs (Beverly, Mass.).

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

More specifically, after a suitable library of peptides has been generated or purchased, the library is then contacted with an appropriate amount of the test substrate, specifically a body surface sample. The library of peptides is dissolved in a suitable solution for contacting the sample. The body surface sample may be suspended in the solution or may be immobilized on a plate or bead. A preferred solution is a buffered aqueous saline solution containing a surfactant. A suitable solution is Tris-buffered saline (TBS) with 0.5% Tween® 20. The solution may additionally be agitated by any means in order to increase the mass transfer rate of the peptides to body surface sample, thereby shortening the time required to attain maximum binding.

Upon contact, a number of the randomly generated peptides will bind to the body surface sample to form a peptide-body-surface complex, for example a peptide-hair, peptide-skin, peptide-nail, or peptide-tooth complex. Unbound peptide may be removed by washing. After all unbound material is removed, peptides having varying degrees of binding affinities for the test surface may be fractionated by selected washings in buffers having varying stringencies. Increasing the stringency of the buffer used increases the required strength of the bond between the peptide and body surface in the peptide-body surface complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P-40, Triton X-100, Tween® 20, wherein Tween® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that peptides having increasing binding affinities for body surface substrates may be eluted by repeating the selection process using buffers with increasing stringencies. The eluted peptides can be identified and sequenced by any means known in the art.

Thus, the following method for generating the body surface-binding peptides, for example, hair-binding peptides, skin-binding peptides, nail-binding peptides, or tooth-binding peptides, may be used. A library of combinatorially generated phage-peptides is contacted with the body surface of interest, to form phage peptide-body surface complexes. The phage-peptide-body-surface complex is separated from uncomplexed peptides and unbound substrate, and the bound phage-peptides from the phage-peptide-body surface complexes is eluted from the complex, preferably by acid treatment. Then, the eluted phage-peptides are identified and sequenced. To identify peptide sequences that bind to one substrate but not to another, for example peptides that bind to hair, but not to skin or peptides that bind to skin, but not to hair, a subtractive panning step is added. Specifically, the library of combinatorially generated phage-peptides is first contacted with the non-target to remove phage-peptides that bind to it. Then, the non-binding phage-peptides are contacted with the desired substrate and the above process is followed. Alternatively, the library of combinatorially generated phage-peptides may be contacted with the non-target and the desired substrate simultaneously. Then, the phage-peptide-body surface complexes are separated from the phage-peptide-non-target complexes and the method described above is followed for the desired phage-peptide-body surface complexes.

In one embodiment, a modified phage display screening method for isolating peptides with a higher affinity for body surfaces is used. In the modified method, the phage-peptide-body surface complexes are formed as described above. Then, these complexes are treated with an elution buffer. Any of the elution buffers described above may be used. Preferably, the elution buffer is an acidic solution. Then, the remaining, elution-resistant phage-peptide-body surface complexes are used to directly infect a bacterial host cell, such as E. coli ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and are sequenced to identify the peptide sequences with a high binding affinity for the body surface of interest.

In another embodiment, PCR may be used to identify the elution-resistant phage-peptides from the modified phage display screening method, described above, by directly carrying out PCR on the phage-peptide-body surface complexes using the appropriate primers, as described by Janssen et al. in U.S. Patent Application Publication No. 2003/0152976, which is incorporated herein by reference.

Hair-binding, skin-binding, and nail-binding peptides have been identified using the above methods, as described by Huang et al. in copending and commonly owned U.S. Patent Application Publication No. 2005/0050656, and U.S. Patent Application Publication No. 2005/0226839, both of which are incorporated herein by reference. Specifically, binding peptides were isolated that have a high affinity for normal brown hair, given as SEQ ID NOs:3-18, 28-38, 40-56, and 64; shampoo resistant peptides having affinity for normal brown hair, given as SEQ ID NO:66, 69 and 70; bleached hair, given as SEQ ID NOs:7, 8, 19-27, 38-40, 43, 44, 47, 57, 58, and 59, fingernail, given as SEQ ID NOs:53 and 60; and skin, given as SEQ ID NO:61. Additionally, the fingernail-binding peptides were found to bind to bleached hair and may be used in the peptide-based hair reagents of the invention. The bleached hair-binding peptides will bind to fingernails and may be used in the peptide-based nail reagents of the invention.

Alternatively, hair and skin-binding peptide sequences may be generated empirically by designing peptides that comprise positively charged amino acids, which can bind to hair and skin via electrostatic interaction, as described by Rothe et al. (WO 2004/000257). The empirically generated hair and skin-binding peptides have between about 4 amino acids to about 50 amino acids, preferably from about 4 to about 25 amino acids, and comprise at least about 40 mole % positively charged amino acids, such as lysine, arginine, and histidine. Peptide sequences containing tripeptide motifs such as HRK, RHK, HKR, RKH, KRH, KHR, HKX, KRX, RKX, HRX, KHX and RHX are most preferred where X can be any natural amino acid but is most preferably selected from neutral side chain amino acids such as glycine, alanine, proline, leucine, isoleucine, valine and phenylalanine. In addition, it should be understood that the peptide sequences must meet other functional requirements in the end use including solubility, viscosity and compatibility with other components in a formulated product and will therefore vary according to the needs of the application. In some cases the peptide may contain up to 60 mole % of amino acids not comprising histidine, lysine or arginine. Suitable empirically generated hair-binding and skin peptides include, but are not limited to, SEQ ID NOs:105-109.

Pigment-Binding Peptides

Pigment-binding peptides (PBP) as defined herein are peptide sequences that specifically bind with high affinity to pigments. The pigment-binding peptides are from about 5 amino acids to 50 amino acids, more preferably, from about 7 amino acids to about 12 amino acids in length.

Suitable pigment-binding peptide sequences may be selected using methods that are well known in the art. For example, pigment-binding peptides may be generated randomly and then selected against a specific pigment based upon their binding affinity for the pigment of interest, as described by O'Brien et al. in U.S. Patent Application Publication No. 2005/0054752, incorporated herein by reference. That method is similar to that described above for the selection of body surface-binding peptides.

As used herein, the term "pigment" means an insoluble colorant. A wide variety of organic and inorganic pigments alone or in combination may be used in the present invention. Examples of suitable pigments include, but are not limited to D&C Red No. 36, D&C Red No. 30, D&C Orange No. 17, Green 3 Lake, Ext. Yellow 7 Lake, Orange 4 Lake, and Red 28 Lake; the calcium lakes of D&C Red Nos. 7, 11, 31 and 34, the barium lake of D&C Red No. 12, the strontium lake D&C Red No. 13, the aluminum lakes of FD&C Yellow No. 5, of FD&C Yellow No. 6, of FD&C No. 40, of D&C Red Nos. 21, 22, 27, and 28, of FD&C Blue No. 1, of D&C Orange No. 5, of D&C Yellow No. 10, the zirconium lake of D&C Red No. 33; Cromophthal® Yellow 131AK (Ciba Specialty Chemicals), Sunfast® Magenta 122 (Sun Chemical) and Sunfast® Blue 15:3 (Sun Chemical), iron oxides, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide, titanium dioxide nanoparticles, zinc oxide, barium oxide, ultramarine blue, bismuth citrate, and white minerals such as hydroxyapatite, and Zircon (zirconium silicate), and carbon black particles.

Examples of suitable pigment-binding peptides include, but are not limited to, those described by O'Brien et al., supra, that have a high affinity for the pigments carbon black, given as SEQ ID NOs:110-113, Cromophthal® Yellow, given as SEQ ID NOs:114-122, Sunfast® Magenta, given as SEQ ID NOs:123-125, and Sunfast® Blue, given as SEQ ID NOs:122, 126-134, and those described by Nomoto et al. in EP1275728 that have a high affinity for carbon black, copper phthalocyanine, titanium dioxide, and silicon dioxide.

Production of Binding Peptides

The body surface-binding peptides and pigment-binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides of the present invention may be prepared using recombinant DNA and molecular cloning techniques. Genes encoding the hair-binding, skin-binding or nail-binding peptides may be produced in heterologous host cells, particularly in the cells of microbial hosts.

Preferred heterologous host cells for expression of the binding peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the peptides of the present invention. Such vectors include, but are not limited to, chromosomal, episomal and virus-derived vectors, e.g., vectors derived from bacterial plasmids, from bacteriophage, from transposons, from insertion elements, from yeast episoms, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the binding peptides of the present invention. These chimeric genes could then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*.

Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence as described supra, as well as an appropriate promoter or control sequence, may be employed to transform an appropriate host to permit the host to express the peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Diblock and Triblock Peptide-Based Body Surface Coloring Reagents

The peptide-based diblock and triblock peptide-based body surface coloring reagents of the present invention are formed by coupling at least one body surface-binding peptide to at least one pigment-binding peptide, either directly or through a molecular spacer. The body surface-binding peptide part of the reagent binds strongly to the body surface, while the pigment-binding sequence binds strongly to the pigment, thereby attaching the pigment to the body surface. The diblock and triblock peptide-based body surface coloring reagents of the invention are from about 14 to about 200 amino acids in length, preferably about 30 to about 130 amino acids in length.

Suitable body surface-binding peptides are described above and include, but are not limited to hair-binding, skin-binding, nail-binding, and tooth-binding peptides selected by the screening methods described above, and empirically generated hair and skin-binding peptides, as described above. Additionally, any known body surface binding peptide may be used, including hair-binding peptides such as SEQ ID NO:1, and skin-binding peptides such as SEQ ID NO:2, described by Janssen et al. in U.S. Patent Application Publication No. 2003/0152976, and hair-binding peptides such as SEQ ID NOs:76-98, and skin-binding peptides such as SEQ ID NOs:99-104, described by Janssen et al. in WO 04048399, both of which are incorporated herein by reference. Additionally, hair conditioner resistant hair-binding peptides such as SEQ ID NO:75, described by Wang et al. (U.S. Patent Application No. 60/657,496), and hair conditioner and shampoo resistant hair-binding peptides such as SEQ ID NOs:153-156, as described by O'Brien et al. (U.S. patent application Ser. No. 11/251,715), may be used.

Suitable pigment-binding peptides are described above and include pigment-binding peptides selected by the screening methods described above. Additionally, any known pigment-binding peptide may be used, such as the peptides that bind to carbon black, copper phthalocyanine, titanium dioxide, and silicon dioxide, described by Nomoto et al. in EP1275728.

The diblock and triblock peptide-based body surface coloring reagents of the present invention are prepared by coupling at least one body surface-binding peptide to at least one pigment-binding peptide, either directly or via an optional spacer. The coupling interaction may be a covalent bond or a non-covalent interaction, such as hydrogen bonding, electrostatic interaction, hydrophobic interaction, or Van der Waals interaction. In the case of a non-covalent interaction, the peptide-based body surface coloring reagents may be prepared by mixing at least one body surface-binding peptide, at least one pigment-binding peptide and the optional spacer (if used) and allowing sufficient time for the interaction to occur. The unbound materials may be separated from the resulting peptide-based body surface coloring reagent using methods known in the art, for example, gel permeation chromatography.

The peptide-based body surface coloring reagents of the invention may also be prepared by covalently attaching at least one body surface-binding peptide to at least one pigment-binding peptide, either directly or through a spacer. Any known peptide or protein conjugation chemistry may be used to form the peptide-based body surface coloring reagents of the invention. Conjugation chemistries are well-known in the art (see for example, Hermanson, *Bioconjugate Techniques*, Academic Press, New York (1996)). Suitable coupling agents include, but are not limited to, carbodiimide coupling agents, diacid chlorides, diisocyanates and other difunctional coupling reagents that are reactive toward terminal amine and/or carboxylic acid groups on the peptides. The preferred coupling agents are carbodiimide coupling agents, such as 1-ethyl-3-(3-dimethylaminopropyl)-carbodiimide (EDC) and N,N'-dicyclohexyl-carbodiimide (DCC), which may be used to activate carboxylic acid groups. Additionally, it may be necessary to protect reactive amine or carboxylic acid groups on the peptides to produce the desired structure for the peptide-based body surface coloring reagent. The use of protecting groups for amino acids, such as t-butyloxycarbonyl (t-Boc), are well known in the art (see for example Stewart et al., supra; Bodanszky, supra; and Pennington et al., supra).

Additionally, diblock peptide-based body surface coloring reagents consisting of at least one body surface binding peptide and at least one pigment-binding peptide may be prepared using the recombinant DNA and molecular cloning techniques described supra.

It may also be desirable to couple the body surface-binding peptide to the pigment-binding peptide via a spacer to form a triblock body surface coloring reagent. The spacer serves to separate the binding peptide sequences to ensure that the binding affinity of the individual peptides is not adversely affected by the coupling. The spacer may also provide other desirable properties such as hydrophilicity, hydrophobicity, or a means for cleaving the peptide sequences to facilitate removal of the coloring agent.

The spacer may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of preferred spacers include, but are not limited to ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl chains, and ethyl, propyl, hexyl, steryl, cetyl, and palmitoyl alkyl chains. The spacer may be covalently attached to the body surface-binding and pigment-binding peptide sequences using any of the coupling chemistries described above. In order to facilitate incorporation of the spacer, a bifunctional cross-linking agent that contains a spacer and reactive groups at both ends for coupling to the peptides may be used. Suitable bifunctional cross-linking agents are well known in the art and include, but are not limited to, diamines, such a as 1,6-diaminohexane; dialdehydes, such as glutaraldehyde; bis N-hydroxysuccinimide esters, such as ethylene glycol-bis (succinic acid N-hydroxysuccinimide ester), disuccinimidyl glutarate, disuccinimidyl suberate, and ethylene glycol-bis (succinimidylsuccinate); diisocyanates, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used. Examples of heterobifunctional cross-linking agents include, but are not limited to compounds having the following structure:

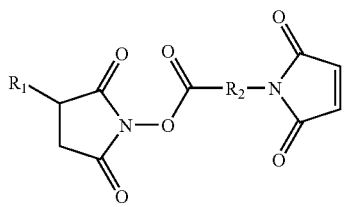

where: $R_1$ is H or a substituent group such as —$SO_3Na$, —$NO_2$, or —Br; and $R_2$ is a spacer such as —$CH_2CH_2$ (ethyl), —$(CH_2)_3$ (propyl), or —$(CH_2)_3C_6H_5$ (propyl phenyl). An example of such a heterobifunctional cross-linking agent is 3-maleimidopropionic acid N-hydroxysuccinimide ester. The N-hydroxysuccinimide ester group of these reagents reacts with amine groups on one peptide, while the maleimide group reacts with thiol groups present on the other peptide. A thiol group may be incorporated into the peptide by adding at least one cysteine group to at least one end of the binding peptide sequence (i.e., the C-terminal end or N-terminal end). Several spacer amino acid residues, such as glycine, may be incorporated between the binding peptide sequence and the terminal cysteine to separate the reacting thiol group from the binding sequence. Moreover, at least one lysine residue may be added to at least one end of the binding peptide sequence, i.e., the C-terminal end or the N-terminal end, to provide an amine group for coupling.

Additionally, the spacer may be a peptide comprising any amino acid and mixtures thereof. The preferred peptide spacers comprise the amino acids glycine, alanine, and serine, and mixtures thereof. In addition, the peptide spacer may contain a specific enzyme cleavage site, such as the protease Caspase 3 site, given by SEQ ID NO:65, which allows for the enzymatic removal of the pigment from the hair. The peptide spacer may be from 1 to about 50 amino acids, preferably from 1 to about 20 amino acids in length. Examples of suitable spacers include, but are not limited to, the sequences given by SEQ ID NOs:135-137. These peptide spacers may be linked to the binding peptide sequences by any method known in the art. For example, the entire triblock peptide-based body surface coloring reagent may be prepared using the standard peptide synthesis methods described supra. In addition, the binding peptides and peptide spacer block may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid groups on the peptides, as described above. Alternatively, the entire triblock peptide-based body surface coloring reagent may be prepared using the recombinant DNA and molecular cloning techniques described supra. The spacer may also be a combination of a peptide spacer and an organic spacer molecule, which may be prepared using the methods described above. Examples of triblock body surface coloring reagents include, but are not limited to, the sequences given as SEQ ID NOs:138-147.

It may also be desirable to have multiple copies of the body surface-binding peptide and the pigment-binding peptide coupled together to enhance the interaction between the peptide-based body surface coloring reagent and the body surface and the pigment, as described by Huang et al. (U.S. Patent Application Publication No. 2005/0050656). Either multiple copies of the same body surface-binding peptide and pigment-binding peptide or a combination of different body surface-binding peptides and pigment-binding peptides may be used. The multi-copy peptide-based body surface coloring reagents may comprise various spacers as described above. Examples of multi-copy body surface-binding peptide-pigment-binding peptide body surface coloring reagents include, but are not limited to, the sequences given as SEQ ID NOs:144, 145, and 147.

In one embodiment of the invention, the peptide-based body surface coloring reagent is a diblock composition comprising a body surface-binding peptide (BSBP) and a pigment-binding peptide (PBP), having the general structure $[(BSBP)_m\text{-}(PBP)_n]_x$, where n and m independently range from 1 to about 10, preferably from 1 to about 5, and x may be 1 to about 10.

In another embodiment, the peptide-based body surface coloring reagent comprises a molecular spacer (S) separating the body surface-binding peptide from the pigment-binding peptide, as described above. Multiple copies of the body surface-binding peptide and the pigment-binding peptide may also be used and the multiple copies of the body surface-binding peptide and the pigment-binding peptide may be separated from themselves and from each other by molecular spacers. In this embodiment, the peptide-based body surface coloring reagent is a triblock composition comprising a body surface-binding peptide, a spacer, and pigment-binding peptide, having the general structure $[[(BSBP)_m\text{-}S_q]_x\text{-}[(PBP)_n\text{-}S_r]_z]_y$, where n, m, x, and z independently range from 1 to about 10, y is from 1 to about 5, and where q and r are each independently 0 or 1, provided that both q and r are not 0. Preferably, m and n independently range from 1 to about 5, and x and z range from 1 to about 3.

In another embodiment, the body surface-binding peptide is a hair-binding peptide and the peptide-based body surface coloring reagent is a diblock composition comprising the hair-binding peptide (HBP) and a pigment-binding peptide (PBP), having the general structure $[(HBP)_m\text{-}(PBP)_n]_x$ where n and m independently range from 1 to about 10, preferably from 1 to about 5, and x may be 1 to about 10.

In another embodiment, the body surface-binding peptide is a hair-binding peptide and the peptide-based body surface coloring reagent is a triblock composition comprising the hair-binding peptide (HBP), a spacer (S), and a pigment-binding peptide (PBP), having the general structure $[[(HBP)_m\text{-}S_q]_x\text{-}[(PBP)_n\text{-}S_r]_z]_y$, where n, m, x, and z independently range from 1 to about 10, y is from 1 to about 5, and where q and r are each independently 0 or 1, provided that both q and r are not 0. Preferably, m and n independently range from 1 to about 5, and x and z range from 1 to about 3.

In another embodiment, the body surface-binding peptide is a skin-binding peptide and the peptide-based body surface coloring reagent is a diblock composition comprising the skin-binding peptide (SBP) and a pigment-binding peptide (PBP), having the general structure $[(SBP)_m\text{-}(PBP)_n]_x$, where n and m independently range from 1 to about 10, preferably from 1 to about 5, and x may be 1 to about 10.

In another embodiment, the body surface-binding peptide is a skin-binding peptide and the peptide-based body surface coloring reagent is a triblock composition comprising the skin-binding peptide (SBP), a spacer (S), and a pigment-binding peptide (PBP), having the general structure $[[(SBP)_m\text{-}S_q]_x\text{-}[(PBP)_n\text{-}S_r]_z]_y$, where n, m, x, and z independently range from 1 to about 10, y is from 1 to about 5, and where q and r are each independently 0 or 1, provided that both q and r are not 0. Preferably, m and n independently range from 1 to about 5, and x and z range from 1 to about 3.

In another embodiment, the body surface-binding peptide is a nail-binding peptide and the peptide-based body surface coloring reagent is a diblock composition comprising the nail-binding peptide (NBP) and a pigment-binding peptide (PBP), having the general structure $[(NBP)_m\text{-}(PBP)_n]_x$ where n and m independently range from 1 to about 10, preferably from 1 to about 5, and x may be 1 to about 10.

In another embodiment, the body surface-binding peptide is a nail-binding peptide and the peptide-based body surface coloring reagent is a triblock composition comprising the nail-binding peptide (NBP), a spacer (S), and a pigment-binding peptide (PBP), having the general structure $[[(NBP)_m\text{-}S_q]_x\text{-}[(PBP)_n\text{-}S_r]_z]_y$, where n, m, x, and z independently range from 1 to about 10, y is from 1 to about 5, and where q and r are each independently 0 or 1, provided that both q and r are not 0. Preferably, m and n independently range from 1 to about 5, and x and z range from 1 to about 3.

In another embodiment, the body surface-binding peptide is a tooth-binding peptide and the peptide-based body surface coloring reagent is a diblock composition comprising the tooth-binding peptide (TBP) and a pigment-binding peptide (PBP), having the general structure $[(TBP)_m\text{-}(PBP)_n]_x$ where n and m independently range from 1 to about 10, preferably from 1 to about 5, and x may be 1 to about 10.

In another embodiment, the body surface-binding peptide is a tooth-binding peptide and the peptide-based body surface coloring reagent is a triblock composition comprising the tooth-binding peptide (TBP), a spacer (S), and a pigment-binding peptide (PBP), having the general structure $[[(TBP)_m\text{-}S_q]_x\text{-}[(PBP)_n\text{-}S_r]_z]_y$, where n, m, x, and z independently range from 1 to about 10, y is from 1 to about 5, and where q and r are each independently 0 or 1, provided that both q and r are not 0. Preferably, m and n independently range from 1 to about 5, and x and z range from 1 to about 3.

It should be understood that as used herein, BSBP, HBP, SBP, NBP, TBP, and PBP are generic designations and are not meant to refer to a single body surface-binding peptide, hair-binding peptide, skin-binding peptide, nail-binding peptide, tooth-binding or pigment-binding peptide sequence, respectively. Where m or n as used above, is greater than 1, it is well within the scope of the invention to provide for the situation where a series of body surface-binding peptides of different sequences and pigment-binding peptides of different sequences may form a part of the composition. Additionally, S is a generic term and is not meant to refer to a single spacer. Where x and y, as used above for the triblock compositions, are greater than 1, it is well within the scope of the invention to provide for the situation where a series of different spacers may form a part of the composition. It should also be understood that these structures do not necessarily represent a covalent bond between the peptides and the optional molecular spacer. As described above, the coupling interaction between the peptides and the optional spacer may be either covalent or non-covalent.

Personal Care Compositions

The diblock and triblock peptide-based body surface coloring reagents of the invention may be used in personal care compositions in conjunction with one or more pigments to color body surfaces, such as hair, skin, nails, and teeth. The body surface-binding peptide block of the peptide-based body surface coloring agent has an affinity for the body surface, while the pigment-binding peptide block has an affinity for the pigment used, thereby attaching the pigment to the body surface. The peptide-based body surface coloring reagent may be present in the same composition as the pigment, or the peptide-based body surface coloring reagent and the pigment may be present in two different personal care compositions that are applied to the body surface in any order, as described below. Personal care compositions include, but are not limited to, hair care compositions, hair coloring compositions, skin care compositions, cosmetic compositions, nail polish compositions, and oral care compositions.

Hair Care Compositions

In one embodiment, the peptide-based body surface coloring reagent is a component of a hair care composition and the peptide-based body surface coloring reagent comprises at least one hair-binding peptide. Hair care compositions are herein defined as compositions for the treatment of hair including, but not limited to, shampoos, conditioners, rinses, lotions, aerosols, gels, and mousses. An effective amount of the peptide-based body surface coloring reagent for use in hair care compositions is a concentration of about 0.01% to about 10%, preferably about 0.01% to about 5% by weight relative to the total weight of the composition. This proportion may vary as a function of the type of hair care composition. Additionally, the hair care composition may further comprise at least one pigment. Suitable pigments are described above. The concentration of the peptide-based body surface coloring reagent in relation to the concentration of the pigment may need to be optimized for best results. Additionally, a mixture of different peptide-based body surface coloring reagents having an affinity for different pigments may be used in the composition. The peptide-based body surface coloring reagents in the mixture need to be chosen so that there is no interaction between the peptides that mitigates the beneficial effect. Suitable mixtures of peptide-based body surface coloring reagents may be determined by one skilled in the art using routine experimentation. If a mixture of peptide-based body surface coloring reagents is used in the composition, the total concentration of the reagents is about 0.01% to about 10% by weight relative to the total weight of the composition.

The composition may further comprise a cosmetically acceptable medium for hair care compositions, examples of which are described by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight for the aqueous-alcoholic solutions. Additionally, the hair care compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes.

Hair Coloring Compositions

In another embodiment, the peptide-based body surface coloring reagent is a component of a hair coloring composition and the peptide-based body surface coloring reagent comprises at least one hair binding peptide. Hair coloring compositions are herein defined as compositions for the coloring or dyeing of hair, which comprise one or more coloring agents. Coloring agents as herein defined are any dye, pigment, and the like that may be used to change the color of a body surface, such as hair, skin, nails, or teeth. Hair coloring agents are well known in the art (see for example Green et al. supra, *CFTA International Color Handbook*, 2$^{nd}$ ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany).

An effective amount of a peptide-based body surface coloring reagent for use in a hair coloring composition is herein defined as a proportion of from about 0.01% to about 20% by weight relative to the total weight of the composition. Additionally, a mixture of different peptide-based body surface coloring reagents having an affinity for different pigments may be used in the composition. The peptide-based body surface coloring reagents in the mixture need to be chosen so that there is no interaction between the peptides that mitigates the beneficial effect. Suitable mixtures of peptide-based body surface coloring reagents may be determined by one skilled in the art using routine experimentation. If a mixture of peptide-based body surface coloring reagents is used in the composition, the total concentration of the reagents is about 0.01% to about 20% by weight relative to the total weight of the composition.

Components of a cosmetically acceptable medium for hair coloring compositions are described by Dias et al., in U.S. Pat. No. 6,398,821 and by Deutz et al., in U.S. Pat. No. 6,129,770, both of which are incorporated herein by reference. For example, hair coloring compositions may contain sequestrants, stabilizers, thickeners, buffers, carriers, surfactants, solvents, antioxidants, polymers, and conditioners.

Skin Care Compositions

In another embodiment, the peptide-based body surface coloring reagent is a component of a skin care composition and the peptide-based body surface coloring reagent comprises at least one skin-binding peptide. Skin care compositions are herein defined as compositions for the treatment of skin including, but not limited to, skin care, skin cleansing, make-up, and anti-wrinkle products. An effective amount of the peptide-based body surface coloring reagent for use in a skin care composition is a concentration of about 0.01% to about 10%, preferably about 0.01% to about 5% by weight relative to the total weight of the composition. This proportion may vary as a function of the type of skin care composition. Additionally, a mixture of different peptide-based body surface coloring reagents having an affinity for different pigments may be used in the composition. The peptide-based body surface coloring reagents in the mixture need to be chosen so that there is no interaction between the peptides that mitigates the beneficial effect. Suitable mixtures of peptide-based body surface coloring reagents may be determined by one skilled in the art using routine experimentation. If a mixture of peptide-based body surface coloring reagents is used in the composition, the total concentration of the reagents is about 0.01% to about 10% by weight relative to the total weight of the composition. The skin care composition may further comprise at least one pigment, suitable examples of which are given above. The concentration of the peptide-based body surface coloring reagent in relation to the concentration of the pigment may need to be optimized for best results.

The composition may further comprise a cosmetically acceptable medium for skin care compositions, examples of which are described by Philippe et al. supra. For example, the cosmetically acceptable medium may be an anhydrous composition containing a fatty substance in a proportion generally of from about 10 to about 90% by weight relative to the total weight of the composition, where the fatty phase contains at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes.

Skin Coloring Compositions

In another embodiment, the peptide-based body surface coloring reagent is a component of a skin coloring composition and the peptide-based body surface coloring reagent comprises at least one skin-binding peptide. The skin coloring composition comprises one or more coloring agents. Any of the coloring agents described above may be used.

The skin coloring compositions may be any cosmetic or make-up product, including but not limited to foundations, blushes, lipsticks, lip liners, lip glosses, eyeshadows and eyeliners. These may be anhydrous make-up products comprising a cosmetically acceptable medium which contains a fatty substance, or they may be in the form of a stable dispersion such as a water-in-oil or oil-in-water emulsion, as described above. In these compositions, an effective amount of the peptide-based body surface coloring reagent is generally from about 0.01% to about 40% by weight relative to the total weight of the composition. Additionally, a mixture of different peptide-based body surface coloring reagents having an affinity for different pigments may be used in the composition. The peptide-based body surface coloring reagents in the mixture need to be chosen so that there is no interaction between the peptides that mitigates the beneficial effect. Suitable mixtures of peptide-based body surface coloring reagents may be determined by one skilled in the art using routine experimentation. If a mixture of peptide-based body surface coloring reagents is used in the composition, the total concentration of the reagents is about 0.01% to about 40% by weight relative to the total weight of the composition.

Cosmetic Compositions

In another embodiment, the peptide-based body surface coloring reagent is a component of a cosmetic composition and the peptide-based body surface coloring reagent comprises at least one hair binding peptide. Cosmetic compositions, as defined herein, are compositions that may be applied to the eyelashes or eyebrows including, but not limited to mascaras, and eyebrow pencils. These cosmetic compositions comprise one or more coloring agents. Any of the coloring agents described above may be used.

An effective amount of a peptide-based body surface coloring reagent for use in a cosmetic composition is herein defined as a proportion of from about 0.01% to about 20% by weight relative to the total weight of the composition. Additionally, a mixture of different peptide-based body surface coloring reagents having affinity for different pigments may be used in the composition. The peptide-based body surface coloring reagents in the mixture need to be chosen so that there is no interaction between the peptides that mitigates the beneficial effect. Suitable mixtures of peptide-based body surface coloring reagents may be determined by one skilled in the art using routine experimentation. If a mixture of peptide-based body surface coloring reagents is used in the composition, the total concentration of the reagents is about 0.01% to about 20% by weight relative to the total weight of the composition.

Cosmetic compositions may be anhydrous make-up products comprising a cosmetically acceptable medium which contains a fatty substance in a proportion generally of from about 10 to about 90% by weight relative to the total weight of the composition, where the fatty phase containing at least one liquid, solid or semi-solid fatty substance, as described above. The fatty substance includes, but is not limited to, oils, waxes, gums, and so-called pasty fatty substances. Alternatively, these compositions may be in the form of a stable dispersion such as a water-in-oil or oil-in-water emulsion, as described above.

Nail Polish Compositions

In another embodiment, the peptide-based body surface coloring reagent is a component of a nail polish composition and the peptide-based body surface coloring reagent comprises at least one nail-binding peptide. The nail polish compositions are used for coloring fingernails and toenails and comprise one or more coloring agents. Any of the coloring agents described above may be used.

An effective amount of a peptide-based body surface coloring reagent for use in a nail polish composition is herein defined as a proportion of from about 0.01% to about 20% by weight relative to the total weight of the composition. Additionally, a mixture of different peptide-based body surface coloring reagents having affinity for different pigments may be used in the composition. The peptide-based body surface coloring reagents in the mixture need to be chosen so that there is no interaction between the peptides that mitigates the beneficial effect. Suitable mixtures of peptide-based body surface coloring reagents may be determined by one skilled in the art using routine experimentation. If a mixture of peptide-based body surface coloring reagents is used in the composition, the total concentration of the reagents is about 0.01% to about 20% by weight relative to the total weight of the composition.

Components of a cosmetically acceptable medium for nail polish compositions are described by Philippe et al. supra. The nail polish composition typically contains a solvent and a film forming substance, such as cellulose derivatives, polyvinyl derivatives, acrylic polymers or copolymers, vinyl copolymers and polyester polymers. Additionally, the nail polish may contain a plasticizer, such as tricresyl phosphate, benzyl benzoate, tributyl phosphate, butyl acetyl ricinoleate, triethyl citrate, tributyl acetyl citrate, dibutyl phthalate or camphor.

Oral Care Compositions

In another embodiment, the peptide-based body surface coloring reagent is a component of an oral care composition and the peptide-based body surface coloring reagent comprises at least one tooth-binding peptide. The oral care compositions of the invention comprise at least one white colorant and are used to whiten teeth. Suitable white colorants which may be used in the oral care composition include, but are not limited to, white pigments such as titanium dioxide and titanium dioxide nanoparticles; and white minerals such as hydroxyapatite, and Zircon (zirconium silicate).

The oral care compositions of the invention may be in the form of powder, paste, gel, liquid, ointment, or tablet. Exemplary oral care compositions include, but are not limited to, toothpaste, dental cream, gel or tooth powder, mouth wash, breath freshener, and dental floss. The oral care compositions comprise an effective amount of the peptide-based body surface coloring reagent of the invention in an orally acceptable carrier medium. An effective amount of a peptide-based body surface coloring reagent for use in an oral care composition may vary depending on the type of product. Typically, the effective amount of the peptide-based body surface coloring reagent is a proportion from about 0.01% to about 90% by weight relative to the total weight of the composition. Additionally, a mixture of different peptide-based body surface coloring reagents having affinity for different pigments may be used in the composition. The peptide-based body surface coloring reagents in the mixture need to be chosen so that there is no interaction between the peptides that mitigates the beneficial effect. Suitable mixtures of peptide-based body surface coloring reagents may be determined by one skilled in the art using routine experimentation. If a mixture of peptide-based body surface coloring reagents is used in the composition, the total concentration of the reagents is about 0.001% to about 90% by weight relative to the total weight of the composition.

Components of an orally acceptable carrier medium are described by White et al. in U.S. Pat. No. 6,740,311; Lawler et al. in U.S. Pat. No. 6,706,256; and Fuglsang et al. in U.S. Pat. No. 6,264,925; all of which are incorporated herein by reference. For example, the oral care composition may comprise one or more of the following: abrasives, surfactants, chelating agents, fluoride sources, thickening agents, buffering agents, solvents, humectants, carriers, bulking agents, and oral benefit agents, such as enzymes, anti-plaque agents, anti-staining agents, anti-microbial agents, anti-caries agents, flavoring agents, coolants, and salivating agents.

Methods for Coloring a Body Surface

The peptide-based body surface coloring reagents of the invention may be used in conjunction with one or more pigments to color body surfaces, such as hair, skin, nails, and teeth. The body surface-binding peptide block of the peptide-based body surface coloring agent has an affinity for the body surface, while the pigment-binding peptide block has an affinity for the pigment used. The peptide-based body surface coloring reagent may be present in the same composition as the pigment, or the peptide-based body surface coloring reagent and the pigment may be present in two different compositions. In one embodiment, a personal care composition comprising at least one peptide-based body surface coloring agent and at least one pigment is applied to a body surface for a time sufficient for the peptide-based body surface coloring agent, which is coupled to the pigment via the pigment-binding peptide block, to bind to the body surface. In another embodiment, at least one pigment is applied to a body surface prior to the application of a composition comprising at least one peptide-based body surface coloring reagent. In another embodiment, a composition comprising at least one peptide-based body surface coloring reagent is applied to the body surface prior to the application of at least one pigment. In another embodiment, at least one pigment and a composition comprising at least one peptide-based body surface coloring reagent are applied to the body surface concomitantly. Optionally, the composition comprising the peptide-based body surface coloring reagent may be reapplied to the body surface after the application of the pigment and the initial application of the composition comprising the peptide-based body surface coloring reagent. Additionally, a composition comprising a polymeric sealant may be applied to the body surface after the application of the pigment and the composition comprising a peptide-based body surface coloring reagent.

Methods for Coloring Hair

The peptide-based body surface coloring reagents of the invention may be used to attach a pigment to the surface of the hair, thereby coloring the hair. The peptide-based body surface coloring reagent and the pigment may be applied to the hair from any suitable hair care composition, for example a hair colorant or hair conditioner composition. These hair care compositions are well known in the art and suitable compositions are described above.

In one embodiment, a pigment is applied to the hair for a time sufficient for the pigment to bind to the hair, typically between about 5 seconds to about 60 minutes. Optionally, the hair may be rinsed to remove the pigment that has not bound to the hair. Then, a composition comprising a peptide-based body surface coloring reagent is applied to the hair for a time sufficient for the body surface coloring reagent to bind to the hair and the pigment, typically between about 5 seconds to about 60 minutes. The composition comprising the peptide-based body surface coloring reagent may be rinsed from the hair or left on the hair.

In another embodiment, a composition comprising a peptide-based body surface reagent is applied to the hair for a time sufficient for the hair-binding peptide block of the body surface coloring reagent to bind to the hair, typically between about 5 seconds to about 60 minutes. Optionally, the hair may be rinsed to remove the composition that has not bound to the hair. Then, a pigment is applied to the hair for a time sufficient for the pigment to bind to the pigment-binding block of the body surface coloring reagent, typically between about 5 seconds to about 60 minutes. The unbound pigment may be rinsed from the hair or left on the hair.

In another embodiment, a pigment and a composition comprising a peptide-based body surface coloring reagent are applied to the hair concomitantly for a time sufficient for the body surface coloring reagent to bind to hair and the pigment, typically between about 5 seconds to about 60 minutes. Optionally, the hair may be rinsed to remove the unbound pigment and the composition comprising a peptide-based body surface coloring reagent from the hair.

In another embodiment, a pigment is provided as part of a composition comprising a peptide-based body surface coloring reagent, for example a hair coloring composition. The composition comprising the pigment and the body surface coloring reagent is applied to the hair for a time sufficient for the body surface coloring reagent, which is coupled to the pigment through the pigment-binding peptide block, to bind to the hair, typically between about 5 seconds to about 60 minutes. The composition comprising the pigment and the body surface coloring reagent may be rinsed from the hair or left on the hair.

In any of the methods described above, the composition comprising a peptide-based body surface coloring reagent may be optionally reapplied to the hair after the application of the pigment and the initial application of the composition comprising a peptide-based body surface coloring reagent in order to further enhance the durability of the colorant.

Additionally, in any of the methods described above, a composition comprising a polymeric sealant may be optionally applied to the hair after the application of the pigment and the composition comprising a peptide-based body surface coloring reagent in order to further enhance the durability of the colorant. The composition comprising the polymeric sealant may be an aqueous solution or a hair care composition, such as a conditioner or rinse, comprising the polymeric sealant. Typically, the polymeric sealant is present in the composition at a concentration of about 0.25% to about 10% by weight relative to the total weight of the composition. Polymeric sealants are well know in the art of personal care products and include, but are not limited to, poly(allylamine), acrylates, acrylate copolymers, polyurethanes, carbomers, methicones, amodimethicones, polyethylenene glycol, beeswax, siloxanes, and the like. The choice of polymeric sealant depends on the particular pigment and the peptide-based body surface coloring reagent used. The optimum polymeric sealant may be readily determined by one skilled in the art using routine experimentation.

Methods for Coloring Skin

The peptide-based body surface coloring reagents of the invention may be used to attach a pigment to the surface of the skin, thereby coloring the skin. The peptide-based body surface coloring reagent and the pigment may be applied to the skin from any suitable skin care composition, for example a skin colorant or skin conditioner composition. These skin care compositions are well known in the art and suitable compositions are described above.

In one embodiment, a pigment is applied to the skin for a time sufficient for the pigment to bind to the skin, typically between about 5 seconds to about 60 minutes. Optionally, the skin may be rinsed to remove the pigment that has not bound to the skin. Then, a composition comprising a peptide-based body surface coloring reagent is applied to the skin for a time sufficient for the body surface coloring reagent to bind to the skin and the pigment, typically between about 5 seconds to about 60 minutes. The composition comprising the peptide-based body surface coloring reagent may be rinsed from the skin or left on the skin.

In another embodiment, a composition comprising a peptide-based body surface coloring reagent is applied to the skin for a time sufficient for the skin-binding peptide block of the body surface coloring reagent to bind to the skin, typically between about 5 seconds to about 60 minutes. Optionally, the skin may be rinsed to remove the composition that has not bound to the skin. Then, a pigment is applied to the skin for a time sufficient for the pigment to bind to the pigment-binding block of the body surface coloring reagent, typically between about 5 seconds to about 60 minutes. The unbound pigment may be rinsed from the skin or left on the skin.

In another embodiment, a pigment and a composition comprising a peptide-based body surface coloring reagent are applied to the skin concomitantly for a time sufficient for the body surface coloring reagent to bind to skin and the pigment, typically between about 5 seconds to about 60 minutes. Optionally, the skin may be rinsed to remove the unbound pigment and the composition comprising a peptide-based body surface coloring reagent from the skin.

In another embodiment, a pigment is provided as part of the composition comprising a peptide-based body surface coloring reagent, for example a skin coloring composition. The composition comprising the pigment and the body surface coloring reagent is applied to the skin for a time sufficient for the body surface coloring reagent, which is coupled to the pigment through the pigment-binding block, to bind to the skin, typically between about 5 seconds to about 60 minutes. The composition comprising the pigment and the body surface coloring reagent may be rinsed from the skin or left on the skin.

In any of the methods described above, the composition comprising a peptide-based body surface coloring reagent may be optionally reapplied to the skin after the application of the pigment and the initial application of the composition comprising a peptide-based body surface coloring reagent in order to further enhance the durability of the colorant.

Additionally, in any of the methods described above, a composition comprising a polymeric sealant may be optionally applied to the skin after the application of the pigment and the composition comprising a peptide-based body surface coloring reagent in order to further enhance the durability of the colorant. Any of the polymeric sealants described above for hair coloring may be used in the form of an aqueous solution or a skin care composition.

Methods for Coloring Nails, Eyebrows, Eyelashes, and Teeth

The methods described above for coloring hair and skin may also be applied to coloring finger nails and toenails, eyebrows, eyelashes, and teeth by applying the appropriate composition, specifically, a nail polish composition, a cosmetic composition, or an oral care composition, to the body surface of interest.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "g" means the gravitation constant, "rpm" means revolutions per minute, "pfu" means plague forming unit, "BSA" means bovine serum albumin, "ELISA" means enzyme linked immunosorbent assay, "IPTG" means isopropyl β-D-thiogalactopyranoside, "A" means absorbance, "$A_{450}$" means the absorbance measured at a wavelength of 450 nm, "$OD_{600}$" means the optical density measured at 600 nanometers, "TBS" means Tris-buffered saline, "TBST-X" means Tris-buffered saline containing Tween® 20 where "X" is the weight percent of Tween® 20, "Xgal" means 5-bromo-4-chloro-3-indolyl-beta-D-galactopyranoside, "SEM" means standard error of the mean, "ESCA" means electron spectroscopy for chemical analysis, "eV" means electron volt(s), "TGA" means thermogravimetric analysis, "GPC" means gel permeation chromatography, "MW" means molecular weight, "$M_w$" means weight-average molecular weight, "vol %" means volume percent, "wt %" means weight percent, "NMR" means nuclear magnetic resonance spectroscopy, "MALDI mass spectrometry" means matrix assisted, laser desorption ionization mass spectrometry, "atm" means atmosphere(s), "kPa" means kilopascal(s), "SLPM" means standard liter per minute, "psi" means pounds per square inch, "RCF" means relative centrifugal field.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1

Selection of Hair-Binding Phage Peptides Using Standard Biopanning

The purpose of this Example was to identify hair-binding phage peptides that bind to normal hair and to bleached hair using standard phage display biopanning.

Phage Display Peptide Libraries:

The phage libraries used in the present invention, Ph.D.-12™ Phage Display Peptide Library Kit and Ph.D.-7™ Phage Display Library Kit, were purchased from New England BioLabs (Beverly, Mass.). These kits are based on a combinatorial library of random peptide 7 or 12-mers fused to a minor coat protein (pIII) of M13 phage. The displayed peptide is expressed at the N-terminus of pIII, such that after the signal peptide is cleaved, the first residue of the coat protein is the first residue of the displayed peptide. The Ph.D.-7 and Ph.D.-12 libraries consist of approximately $2.8 \times 10^9$ and $2.7 \times 10^9$ sequences, respectively. A volume of 10 μL contains about 55 copies of each peptide sequence. Each initial round of experiments was carried out using the original library provided by the manufacturer in order to avoid introducing any bias into the results.

Preparation of Hair Samples:

The samples used as normal hair were 6-inch medium brown human hairs obtained from International Hair Importers and Products (Bellerose, N.Y.). The hairs were placed in 90% isopropanol for 30 min at room temperature and then washed 5 times for 10 min each with deionized water. The hairs were air-dried overnight at room temperature.

To prepare the bleached hair samples, the medium brown human hairs were placed in 6% $H_2O_2$, which was adjusted to pH 10.2 with ammonium hydroxide, for 10 min at room temperature and then washed 5 times for 10 min each with deionized water. The hairs were air-dried overnight at room temperature.

The normal and bleached hair samples were cut into 0.5 to 1 cm lengths and about 5 to 10 mg of the hairs was placed into wells of a custom 24-well biopanning apparatus that had a pig skin bottom. An equal number of the pig skin bottom wells were left empty. The pig skin bottom apparatus was used as a subtractive procedure to remove phage-peptides that have an affinity for skin. This apparatus was created by modifying a dot blot apparatus (obtained from Schleicher & Schuell, Keene, N.H.) to fit the biopanning process. Specifically, the top 96-well block of the dot blot apparatus was replaced by a 24-well block. A 4×6 inch treated pig skin was placed under the 24-well block and panning wells with a pig skin bottom were formed by tightening the apparatus. The pig skin was purchased from a local supermarket and stored at −80° C. Before use, the skin was placed in deionized water to thaw, and then blotted dry using a paper towel. The surface of the skin was wiped with 90% isopropanol, and then rinsed with deionized water. The 24-well apparatus was filled with blocking buffer consisting of 1 mg/mL BSA in TBST containing 0.5% Tween® 20 (TBST-0.5%) and incubated for 1 h at 4° C. The wells and hairs were washed 5 times with TBST-0.5%. One milliliter of TBST-0.5% containing 1 mg/mL BSA was added to each well. Then, 10 μL of the original phage library ($2 \times 10^{11}$ pfu), either the 12-mer or 7-mer library, was added to the pig skin bottom wells that did not contain a hair sample and the phage library was incubated for 15 min at room temperature. The unbound phages were then transferred to pig skin bottom wells containing the hair samples and were incubated for 15 min at room temperature. The hair samples and the wells were washed 10 times with TBST-0.5%. The hairs were then transferred to clean, plastic bottom wells of a 24-well plate and 1 mL of a non-specific elution buffer consisting of 1 mg/mL BSA in 0.2 M glycine-HCl, pH 2.2, was added to each well and incubated for 10 min to elute the bound phages. Then, 160 μL of neutralization buffer consisting of 1 M Tris-HCl, pH 9.2, was added to each well. The eluted phages from each well were transferred to a new tube for titering and sequencing.

To titer the bound phages, the eluted phage was diluted with SM buffer (100 mM NaCl, 12.3 mM $MgSO_4$-7 $H_2O$, 50 mM Tris-HCl, pH 7.5, and 0.01 wt/vol % gelatin) to prepare 10-fold serial dilutions of $10^1$ to $10^4$. A 10 μL aliquot of each dilution was incubated with 200 μL of mid-log phase E. coli ER2738 (New England BioLabs), grown in LB medium for 20 min and then mixed with 3 mL of agarose top (LB medium with 5 mM $MgCl_2$, and 0.7% agarose) at 45° C. This mixture was spread onto a S-Gal™/LB agar plate (Sigma Chemical Co.) and incubated overnight at 37° C. The S-Gal™/LB agar blend contained 5 g of tryptone, 2.5 g of yeast extract, 5 g of sodium chloride, 6 g of agar, 150 mg of 3,4-cyclohexenoesculetin-β-D-galactopyranoside (S-Gal™), 250 mg of ferric ammonium citrate and 15 mg of isopropyl β-D-thiogalactoside (IPTG) in 500 mL of distilled water. The plates were prepared by autoclaving the S-Gal™/LB for 15 to 20 min at 121-124° C. The single black plaques were randomly picked for DNA isolation and sequence analysis.

The remaining eluted phages were amplified by incubating with diluted E.coli ER2738, from an overnight culture diluted 1:100 in LB medium, at 37° C. for 4.5 h. After this time, the cell culture was centrifuged for 30 s and the upper 80% of the supernatant was transferred to a fresh tube, ⅙ volume of PEG/NaCl (20% polyethylene glyco-800, 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then titered according to the same method as described above. For the next round of biopanning, more than $2 \times 10^{11}$ pfu of phage stock from the first round was used. The biopanning process was repeated for 3 to 6 rounds depending on the experiments.

The single plaque lysates were prepared following the manufacture's instructions (New England Biolabs) and the single stranded phage genomic DNA was purified using the QIAprep Spin M13 Kit (Qiagen, Valencia, Calif.) and sequenced at the DuPont Sequencing Facility using −96 gIII sequencing primer (5'-CCCTCATAGTTAGCGTAACG-3'), given as SEQ ID NO:62. The displayed peptide is located immediately after the signal peptide of gene III.

The amino acid sequences of the eluted normal hair-binding phage peptides from the 12-mer library isolated from the fifth round of biopanning are given in Table 1. The amino acid sequences of the eluted bleached hair-binding phage peptides from the 12-mer library isolated from the fifth round of biopanning are given in Table 2. Repeated amino acid sequences of the eluted normal hair-binding phage peptides from the 7-mer library from 95 randomly selected clones, isolated from the third round of biopanning, are given in Table 3.

TABLE 1

Amino Acid Sequences of Eluted Normal Hair-Binding Phage Peptides from 12-Mer Library

| Clone ID | Amino Acid Sequence | SEQ ID NO: | Frequency[1] |
|---|---|---|---|
| 1 | RVPNKTVTVDGA | 5 | 5 |
| 2 | DRHKSKYSSTKS | 6 | 2 |
| 3 | KNFPQQKEFPLS | 7 | 2 |
| 4 | QRNSPPAMSRRD | 8 | 2 |
| 5 | TRKPNMPHGQYL | 9 | 2 |
| 6 | KPPHLAKLPFTT | 10 | 1 |
| 7 | NKRPPTSHRIHA | 11 | 1 |
| 8 | NLPRYQPPCKPL | 12 | 1 |

TABLE 1-continued

Amino Acid Sequences of Eluted Normal Hair-Binding Phage Peptides from 12-Mer Library

| Clone ID | Amino Acid Sequence | SEQ ID NO: | Frequency[1] |
|---|---|---|---|
| 9 | RPPWKKPIPPSE | 13 | 1 |
| 10 | RQRPKDHFFSRP | 14 | 1 |
| 11 | SVPNKXVTVDGX | 15 | 1 |
| 12 | TTKWRHRAPVSP | 16 | 1 |
| 13 | WLGKNRIKPRAS | 17 | 1 |
| 14 | SNFKTPLPLTQS | 18 | 1 |
| 15 | SVSVGMKPSPRP | 3 | 1 |

[1]The frequency represents the number of identical sequences that occurred out of 23 sequenced clones.

TABLE 2

Amino Acid Sequences of Eluted Bleached Hair-Binding Phage Peptides from 12-Mer Library

| Clone ID | Amino Acid Sequence | SEQ ID NO: | Frequency[1] |
|---|---|---|---|
| 1 | KELQTRNVVQRE | 19 | 8 |
| 2 | QRNSPPAMSRRD | 8 | 5 |
| 3 | TPTANQFTQSVP | 20 | 2 |
| 4 | AAGLSQKHERNR | 21 | 2 |
| 5 | ETVHQTPLSDRP | 22 | 1 |
| 6 | KNFPQQKEFPLS | 7 | 1 |
| 7 | LPALHIQRHPRM | 23 | 1 |
| 8 | QPSHSQSHNLRS | 24 | 1 |
| 9 | RGSQKSKPPRPP | 25 | 1 |
| 10 | THTQKTPLLYYH | 26 | 1 |
| 11 | TKGSSQAILKST | 27 | 1 |

[1]The frequency represents the number of identical sequences that occurred out of 24 sequenced clones.

TABLE 3

Amino Acid Sequences of Eluted Normal Hair-Binding Phage Peptides from 7-Mer Library

| Clone ID | Amino Acid Sequence | SEQ ID NO: |
|---|---|---|
| A | DLHTVYH | 28 |
| B | HIKPPTR | 29 |
| D | HPVWPAI | 30 |
| E | MPLYYLQ | 31 |
| F[1] | HLTVPWRGGGSAVPFYSHSQITLPNH | 32 |
| G[1] | GPHDTSSGGVRPNLHHTSKKEKRENRKVPFYSHSVTSRGNV | 33 |
| H | KHPTYRQ | 34 |

TABLE 3-continued

Amino Acid Sequences of Eluted Normal Hair-Binding Phage Peptides from 7-Mer Library

| Clone ID | Amino Acid Sequence | SEQ ID NO: |
|---|---|---|
| I | HPMSAPR | 35 |
| J | MPKYYLQ | 36 |

[1]There was a multiple DNA fragment intersion in these clones.

Example 2

Selection of High Affinity Hair-Binding Phage Peptides Using a Modified Method

The purpose of this Example was to identify hair-binding phage peptides with a higher binding affinity.

The hairs that were treated with the acidic elution buffer, as described in Example 1, were washed three more times with the elution buffer and then washed three times with TBST-0.5%. These hairs, which had acid resistant phage peptides still attached, were used to directly infect 500 μL of mid-log phase bacterial host cells, E. coli ER2738 (New England BioLabs), which were then grown in LB medium for 20 min and then mixed with 3 mL of agarose top (LB medium with 5 mM $MgCl_2$, and 0.7% agarose) at 45° C. This mixture was spread onto a LB medium/IPTG/S-Gal™ plate (LB medium with 15 g/L agar, 0.05 g/L IPTG, and 0.04 g/L S-Gal™) and incubated overnight at 37° C. The black plaques were counted to calculate the phage titer. The single black plaques were randomly picked for DNA isolation and sequencing analysis, as described in Example 1. This process was performed on the normal and bleached hair samples that were screened with the 7-mer and 12-mer phage display libraries, as described in Example 1. The amino acid sequences of these high affinity, hair-binding phage peptides are given in Tables 4-7.

TABLE 4

Amino Acid Sequences of High Affinity, Normal Hair-Binding Phage Peptides from 7-Mer Library

| Clone ID | Amino Acid Sequence | SEQ ID NO: |
|---|---|---|
| D5 | GPHDTSSGGVRPNLHHTSKKEKRENRKVPFYSHSVTSRGNV[1] | 33 |
| A36 | MHAHSIA | 37 |
| B41 | TAATTSP | 38 |

[1]There was a multiple DNA fragment intersion in this clone.

TABLE 5

Amino Acid Sequences of High Affinity, Bleached Hair-Binding Phage Peptides from 7-Mer Library

| Clone ID | Amino Acid Sequence | SEQ ID NO: |
|---|---|---|
| D39 | LGIPQNL | 39 |
| B1 | TAATTSP | 38 |

TABLE 6

Amino Acid Sequences of High Affinity, Normal Hair-Binding Phage Peptides from 12-Mer Library

| Clone ID | Amino Acid Sequence | SEQ ID NO: |
|---|---|---|
| C2 | AKPISQHLQRGS | 40 |
| A3 | APPTPAAASATT | 41 |
| F9 | DPTEGARRTIMT | 42 |
| A19 | EQISGSLVAAPW | 43 |
| F4 | LDTSFPPVPFHA | 44 |
| F35 | LPRIANTWSPS | 45 |
| D21 | RTNAADHPAAVT | 46 |
| C10 | SLNWVTIPGPKI | 47 |
| C5 | TDMQAPTKSYSN | 48 |
| D20 | TIMTKSPSLSCG | 49 |
| C18 | TPALDGLRQPLR | 50 |
| A20 | TYPASRLPLLAP | 51 |
| C13 | AKTHKHPAPSYS | 52 |
| G-D20 | YPSFSPTYRPAF | 53 |
| A23 | TDPTPFSISPER | 54 |
| F67 | SQNWQDSTSYSN | 55 |
| F91 | WHDKPQNSSKST | 56 |
| G-F1 | LDVESYKGTSMP | 4 |

TABLE 7

Amino Acid Sequences of High Affinity, Bleached Hair-Binding Phage Peptides from 12-Mer Library

| Clone ID | Amino Acid Sequence | SEQ ID NO: |
|---|---|---|
| A5 | EQISGSLVAAPW | 43 |
| C4 | NEVPARNAPWLV | 57 |
| D30 | NSPGYQADSVAIG | 58 |
| C44 | AKPISQHLQRGS | 40 |
| E66 | LDTSFPPVPFHA | 44 |
| C45 | SLNWVTIPGPKI | 47 |
| E18 | TQDSAQKSPSPL | 59 |

Example 3

Selection of High Affinity Fingernail-Binding Phage Peptides

The purpose of this Example was to identify phage peptides that have a high binding affinity to fingernails. The modified biopanning method described in Example 2 was used to identify high affinity, fingernail-binding phage-peptide clones.

Human fingernails were collected from test subjects. The fingernails were cleaned by brushing with soap solution, rinsed with deionized water, and allowed to air-dry at room temperature. The fingernails were then powdered under liquid $N_2$, and 10 mg of the fingernails was added to each well of a 96-well filter plate. The fingernail samples were treated for 1 h with blocking buffer consisting of 1 mg/mL BSA in TBST-0.5%, and then washed with TBST-0.5%. The fingernail samples were incubated with phage library (Ph.D-12 Phage Display Peptide Library Kit), and washed 10 times using the same conditions described in Example 1. After the acidic elution step, described in Example 1, the fingernail samples were washed three more times with the elution buffer and then washed three times with TBST-0.5%. The acid-treated fingernails, which had acid resistant phage peptides still attached, were used to directly infect *E. coli* ER2738 cells as described in Example 2. This biopanning process was repeated three times. A total of 75 single black phage plaques were picked randomly for DNA isolation and sequencing analysis and two repeated clones were identified. The amino acid sequences of these phage peptides are listed in Table 8. These fingernail binding peptides were also found to bind well to bleached hair.

TABLE 8

Amino Acid Sequences of High Affinity Fingernail-Binding Phage Peptides

| Clone ID | Amino Acid Sequence | SEQ ID NO: | Frequency[1] |
|---|---|---|---|
| F01 | ALPRIANTWSPS | 60 | 15 |
| D05 | YPSFSPTYRPAF | 53 | 26 |

[1]The frequency represents the number of identical sequences that occurred out of 75 sequenced clones.

Example 4

Selection of High Affinity Skin-Binding Phage Peptides

The purpose of this Example was to identify phage peptides that have a high binding affinity to skin. The modified biopanning method described in Examples 2 and 4 was used to identify the high affinity, skin-binding phage-peptide clones. Pig skin served as a model for human skin in the process.

The pig skin was prepared as described in Example 1. Three rounds of screenings were performed with the custom, pig skin bottom biopanning apparatus using the same procedure described in Example 4. A total of 28 single black phage plaques were picked randomly for DNA isolation and sequencing analysis and one repeated clone was identified. The amino acid sequence of this phage peptide, which appeared 9 times out of the 28 sequences, was TPFHSPENAPGS, given as SEQ ID NO:61.

Example 5

Quantitative Characterization of the Binding Affinity of Hair-Binding Phage Clones The purpose of this Example was to quantify the binding affinity of phage clones by titering and ELISA.

Titering of Hair-Binding Phage Clones:

Phage clones displaying specific peptides were used for comparing the binding characteristics of different peptide sequences. A titer-based assay was used to quantify the phage binding. This assay measures the output pfu retained by 10 mg of hair surfaces, having a signal to noise ratio of $10^3$ to $10^4$. The input for all the phage clones was $10^{14}$ pfu. It should be emphasized that this assay measures the peptide-expressing phage particle, rather than peptide binding.

Normal hairs were cut into 0.5 cm lengths and 10 mg of the cut hair was placed in each well of a 96-well filter plate (Qiagen). Then, the wells were filled with blocking buffer containing 1 mg/mL BSA in TBST-0.5% and incubated for 1 h at 4° C. The hairs were washed 5 times with TBST-0.5%. The wells were then filled with 1 mL of TBST-0.5% containing 1 mg/mL BSA and then purified phage clones ($10^{14}$ pfu) were added to each well. The hair samples were incubated for 15 min at room temperature and then washed 10 times with TBST-0.5%. The hairs were transferred to a clean well and 1.0 mL of a non-specific elution buffer, consisting of 1 mg/mL BSA in 0.2 M Glycine-HCl at pH 2.2, was added to each well. The samples were incubated for 10 min and then 160 µL of neutralization buffer (1 M Tris-HCl, pH 9.2) was added to each well. The eluted phages from each well were transferred to a new tube for titering and sequencing analysis.

To titer the bound phages, the eluted phage was diluted with SM buffer to prepare 10-fold serial dilutions of $10^1$ to $10^8$. A 10 µL aliquot of each dilution was incubated with 200 µL of mid-log phase *E. coli* ER2738 (New England BioLabs), and grown in LB medium for 20 min and then mixed with 3 mL of agarose top (LB medium with 5 mM $MgCl_2$, and 0.7% agarose) at 45° C. This mixture was spread onto a LB medium/IPTG/Xgal plate (LB medium with 15 g/L agar, 0.05 g/L IPTG, and 0.04 g/L Xgal) and incubated overnight at 37° C. The blue plaques were counted to calculate the phage titers, which are given in Table 9.

TABLE 9

Titer of Hair-Binding Phage Clones

| Clone ID | SEQ ID NO: | Phage Titer |
|---|---|---|
| A | 28 | $7.50 \times 10^4$ |
| B | 29 | $1.21 \times 10^5$ |
| D | 30 | $8.20 \times 10^4$ |
| E | 31 | $1.70 \times 10^5$ |
| F | 32 | $1.11 \times 10^6$ |
| G | 33 | $1.67 \times 10^8$ |
| H | 34 | $1.30 \times 10^6$ |
| 1 | 35 | $1.17 \times 10^6$ |
| J | 36 | $1.24 \times 10^6$ |

Characterization of Hair-Binding Phage Clones by ELISA:

Enzyme-linked immunosorbent assay (ELISA) was used to evaluate the hair-binding specificity of selected phage-peptide clones. Phage-peptide clones identified in Examples 1 and 2 along with a randomly chosen control G-F9, KHGPDLLRSAPR (given as SEQ ID NO:63) were amplified. More than $10^{14}$ pfu phages were added to pre-blocked hair surfaces. The same amount of phages was also added to pre-blocked pig skin surfaces as a control to demonstrate the hair-binding specificity.

A unique hair or pig skin-bottom 96-well apparatus was created by applying one layer of Parafilm® under the top 96-well block of a Minifold I Dot-Blot System (Schleicher & Schuell, Inc., Keene, N.H.), adding hair or a layer of hairless pig skin on top of the Parafilm® cover, and then tightening the apparatus. For each clone to be tested, the hair-covered well was incubated for 1 h at room temperature with 200 µL of blocking buffer, consisting of 2% non-fat dry milk (Schleicher & Schuell, Inc.) in TBS. A second Minifold system with pig skin at the bottom of the wells was treated with blocking buffer simultaneously to serve as a control. The blocking buffer was removed by inverting the systems and blotting them dry with paper towels. The systems were rinsed 6 times with wash buffer consisting of TBST-0.05%. The wells were filled with 200 µL of TBST-0.5% containing 1 mg/mL BSA and then 10 µL (over $10^{12}$ copies) of purified phage stock was added to each Well. The samples were incubated at 37° C. for 15 min with slow shaking. The non-binding phage was removed by washing the wells 10 to 20 times with TBST-0.5%. Then, 100 µL of horseradish peroxidase/anti-M13 antibody conjugate (Amersham USA, Piscataway, N.J.), diluted 1:500 in the blocking buffer, was added to each well and incubated for 1 h at room temperature. The conjugate solution was removed and the wells were washed 6 times with TBST-0.05%. TMB substrate (200 µL), obtained from Pierce Biotechnology (Rockford, Ill.) was added to each well and the color was allowed to develop for between 5 to 30 min, typically for 10 min, at room temperature. Then, stop solution (200 µL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values, reported as the mean of at least three replicates, and the standard error of the mean (SEM) are given in Table 10.

TABLE 10

Results of ELISA Assay with Skin and Hair

| Clone ID | SEQ ID NO: | Hair $A_{450}$ | SEM | Pig Skin $A_{450}$ | SEM |
|---|---|---|---|---|---|
| G-F9 (Control) | 63 | 0.074 | 0.057 | −0.137 | 0.015 |
| D21 | 46 | 1.051 | 0.16 | 0.04 | 0.021 |
| D39 | 39 | 0.685 | 0.136 | 0.086 | 0.019 |
| D5 | 33 | 0.652 | 0.222 | 0.104 | 0.023 |
| A36 | 37 | 0.585 | 0.222 | 0.173 | 0.029 |
| C5 | 48 | 0.548 | 0.263 | 0.047 | 0.037 |
| C10 | 47 | 0.542 | 0.105 | 0.032 | 0.012 |
| A5 | 43 | 0.431 | 0.107 | 0.256 | 0.022 |
| B1 | 38 | 0.42 | 0.152 | 0.127 | 0.023 |
| D30 | 58 | 0.414 | 0.119 | 0.287 | 0.045 |
| C13 | 52 | 0.375 | 0.117 | 0.024 | 0.016 |
| C18 | 50 | 0.34 | 0.197 | 0.132 | 0.023 |

As can be seen from the data in Table 10, all the hair-binding clones had a significantly higher binding affinity for hair than the control. Moreover, the hair-binding clones exhibited various degrees of selectivity for hair compared to pig skin. Clone D21 had the highest selectivity for hair, having a very strong affinity for hair and a very low affinity for pig skin.

Example 6

Confirmation of Peptide Binding Specificity and Affinity

The purpose of this Example was to test the peptide binding site specificity and affinity of the hair-binding peptide D21 using a competition ELISA. The ELISA assay only detects phage particles that remain bound to the hair surface. Therefore, if the synthetic peptide competes with the phage particle for the same binding site on hair surface, the addition of the synthetic peptide into the ELISA system will significantly reduce the ELISA results due to the peptide competition.

The synthetic hair-binding peptide D21, given as SEQ ID NO:46, was synthesized by SynPep (Dublin, Calif.). As a control, an unrelated synthetic skin-binding peptide, given as SEQ ID NO:61, was added to the system. The experimental conditions were similar to those used in the ELISA method described in Example 5. Briefly, 100 μL of Binding Buffer (1× TBS with 0.1% Tween® 20 and 1 mg/mL BSA) and $10^{11}$ pfu of the pure D21 phage particles were added to each well of the 96-well filter plate, which contained a sample of normal hair. The synthetic peptide (100 μg) was added to each well (corresponding to concentration of 0.8 mM). The reactions were carried out at room temperature for 1 h with gentle shaking, followed by five washes with TBST-0.5%. The remaining steps were identical to the those used in the ELISA method described in Example 5. The ELISA results, presented as the absorbance at 450 nm ($A_{450}$), are shown in Table 11. Each individual ELISA test was performed in triplicate; the values in Table 11 are the means of the triplicate determinations.

TABLE 11

Results of Peptide Competition ELISA

| Sample | $A_{450}$ | SEM |
|---|---|---|
| Antibody-Conjugate | 0.199 | 0.031 |
| Phage D21 | 1.878 | 0.104 |
| Phage D21 and D21 Peptide | 1.022 | 0.204 |
| Phage D21 and Control Peptide | 2.141 | 0.083 |

These results demonstrated that the synthetic peptide D21 does compete with the phage clone D21 for the same binding sites on the hair surface.

Example 7

Selection of Shampoo-Resistant Hair-Binding Phage-Peptides Using Biopanning

The purpose of this Example was to select shampoo-resistant hair-binding phage-peptides using biopanning with shampoo washes.

In order to select shampoo-resistant hair-binding peptides, a biopanning experiment using 12-mer phage peptide libraries against normal and bleached hairs was performed, as described in Example 2. Instead of using normal TBST buffer to wash-off the unbounded phages, the phage-complexed hairs were washed with 10%, 30% and 50% shampoo solutions (Pantene Pro-V shampoo, Sheer Volume, Proctor & Gamble, Cincinnati, Ohio), for 5 min in separate tubes, followed by six TBS buffer washes. The washed hairs were directly used to infect host bacterial cells as described in the modified biopanning method, described in Example 2.

A potential problem with this method is the effect of the shampoo on the phage's ability to infect bacterial host cells. In a control experiment, a known amount of phage particles was added to a 10% shampoo solution for 5 min, and then a portion of the solution was used to infect bacterial cells. The titer of the shampoo-treated phage was 90% lower than that of the untreated phage. The 30% and 50% shampoo treatments gave even more severe damage to the phage's ability to infect host cells. Nevertheless, two shampoo-resistant hair-binding phage-peptides were identified, as shown in Table 12.

TABLE 12

Peptide Sequences of Shampoo-Resistant Hair-binding Phage Peptides Identified Using the Biopanning Method

| Clone | Sequence | Target | SEQ ID NO: |
|---|---|---|---|
| I-B5 | TPPELLHGDPRS | Normal and Bleached Hair | 66 |
| H-B1 | TPPTNVLMLATK | Normal Hair | 69 |

Example 8

Selection of Shampoo-Resistant Hair-Binding Phage-Peptides Using PCR

The purpose of this Example was to select shampoo-resistant hair-binding phage-peptides using a PCR method to avoid the problem of shampoo induced damage to the phage. This principle of the PCR method is that DNA fragments inside the phage particle can be recovered using PCR, regardless of the phage's viability, and that the recovered DNA fragments, corresponding to the hair-binding peptide sequences, can then been cloned back into a phage vector and packaged into healthy phage particles.

Biopanning experiments were performed using 7-mer and 12-mer phage-peptide libraries against normal and bleached hairs, as described in Example 1. After the final wash, the phage-treated hairs were subjected to 5 min of shampoo washes, followed by six TBS buffer washes. The shampoo-washed hairs were put into a new tube filled with 1 mL of water, and boiled for 15 min to release the DNA. This DNA-containing, boiled solution was used as a DNA template for PCR reactions. The primers used in the PCR reaction were primers: M13KE-1412 Forward 5'-CAAGC-CTCAGCGACCGAATA-3', given as SEQ ID NO:67 and M13KE-1794 Reverse 5'-CGTAACACTGAGTTTCGT-CACCA-3', given SEQ ID NO:68. The PCR conditions were: 3 min denaturing at 96° C., followed by 35 cycles of 94° C. for 30 sec, 50° C. for 30 sec and 60° C. for 2 min. The PCR products (~400 bp), and M13KE vector (New England BioLabs) were digested with restriction enzymes Eag I and Acc65 I. The ligation and transformation conditions, as described in the Ph.D.™ Peptide Display Cloning System (New England Biolabs), were used. The amino acid sequence of the resulting shampoo-resistant hair-binding phage-peptide is NTSQLST, given as SEQ ID NO:70.

Example 9

Determination of the Affinity of Hair-Binding and Skin-Binding Peptides

The purpose of this Example was to determine the affinity of the hair-binding and skin-binding peptides for their respective substrates, measured as $MB_{50}$ values, using an ELISA assay.

Hair-binding and skin-binding peptides were synthesized by SynPep Inc. (Dublin, Calif.). The peptides were biotinylated by adding a biotinylated lysine residue at the C-terminus of the amino acid binding sequences for detection purposes and an amidated cysteine was added to the C-terminus of the sequence. The amino acid sequences of the peptides tested are given as SEQ ID NOs:71-74, as shown in Table 13.

For hair samples, the procedure used was as follows. The setup of the surface specific 96-well system used was the same as that described in Example 5. Briefly, the 96-wells with hair or pig skin surfaces were blocked with blocking buffer (SuperBlock™ from Pierce Chemical Co., Rockford, Ill.) at room temperature for 1 h, followed by six washes with TBST-0.5%, 2 min each, at room temperature. Various concentrations of biotinylated, binding peptide were added to each well, incubated for 15 min at 37° C., and washed six times with TBST-0.5%, 2 min each, at room temperature. Then, streptavidin-horseradish peroxidase (HRP) conjugate (Pierce Chemical Co.) was added to each well (1.0 µg per well), and incubated for 1 h at room temperature. After the incubation, the wells were washed six times with TBST-0.5%, 2 min each at room temperature. Finally, the color development and the measurement were performed as described in Example 5.

For the measurement of $MB_{50}$ of the peptide-skin complexes, the following procedure was used. First, the pigskin was treated to block the endogenous biotin in the skin. This was done by adding streptavidin to the blocking buffer. After blocking the pigskin sample, the skin was treated with D-biotin to block the excess streptavidin binding sites. The remaining steps were identical to those used for the hair samples.

The results were plotted as $A_{450}$ versus the concentration of peptide using GraphPad Prism 4.0 (GraphPad Software, Inc., San Diego, Calif.). The $MB_{50}$ values were calculated from Scatchard plots and are summarized in Table 13. The results demonstrate that the binding affinity of the hair-binding peptides (D21, F35, and I-B5) and the skin binding peptide (SEQW ID NO:61) for their respective substrate was high, while the binding affinity of the hair-binding peptides (D-21 and I-B5) for skin was relatively low.

TABLE 13

Summary of $MB_{50}$ Values for Hair and Skin-Binding Peptides

| Binding Peptide | Peptide Sequence Tested* | Substrate | $MB_{50}$, M |
| --- | --- | --- | --- |
| D21 | SEQ ID NO: 71 | Normal Hair | $2 \times 10^{-6}$ |
| F35 | SEQ ID NO: 72 | Bleached Hair | $3 \times 10^{-6}$ |
| I-B5 | SEQ ID NO: 73 | Normal and Bleached Hair | $3 \times 10^{-7}$ |
| D21 | SEQ ID NO: 71 | Pig Skin | $4 \times 10^{-5}$ |
| I-B5 | SEQ ID NO: 73 | Pig Skin | $>1 \times 10^{-4}$ |
| SEQ ID NO: 61 | SEQ ID NO: 74 | Pig Skin | $7 \times 10^{-7}$ |

*The peptides tested were biotinylated at the C-terminus of the amino acid binding sequences and an amidated cysteine was added to the C-terminus of the binding sequence.

Example 10

Selection of Tooth-Binding Peptides Using Biopanning

The purpose of this prophetic Example is to describe how to identify phage peptides that bind to teeth with high affinity.

Extracted human teeth, which may be obtained from a Dental Office, are cleaned by brushing with soap solution, rinsed with deionized water, and allowed to air-dry at room temperature. The teeth are placed in a 15 mL centrifuge tube (Corning Inc., Acton, Mass.), one tooth per tube. The teeth samples are treated for 1 h with blocking buffer consisting of 1 mg/mL BSA in TBST-0.5%, and then washed with TBST-0.5%. The teeth samples are incubated with the phage library (Ph.D-12 Phage Display Peptide Library Kit) and washed 10 times using the same conditions described in Example 1. After the acidic elution step, described in Example 1, the teeth samples are washed three more times with the elution buffer and then washed three times with TBST-0.5%. The acid-treated teeth, which have acid resistant phage peptides still attached, are used to directly infect E. coli ER2738 cells as described in Example 2. The amplified and isolated phages are contacted with a fresh tooth sample and the biopanning procedure is repeated two more times. After the third round of biopanning, the acid-treated teeth are used to directly infect E. coli ER2738 cells, and the cells are cultured as described in Example 1. Single black plaques are randomly picked for DNA isolation and sequence analysis. The single plaque lysates are prepared following the manufacture's instructions (New England Biolabs) and the single stranded phage genomic DNA is purified using the QIAprep Spin M13 Kit (Qiagen, Valencia, Calif.) and sequenced using −96 glll sequencing primer, as described in Example 1.

The identified peptide sequences will have a binding affinity for teeth. The binding specificity and affinity of the identified tooth-binding peptides is determined as described in Example 6.

Examples 11-16

Hair Coloring Using Triblock Peptide-Based Body Surface Coloring Reagents

The purpose of these Examples was to demonstrate the coloring of hair using triblock peptide-based body surface coloring reagents in combination with a carbon black pigment. The triblock peptide-based body surface coloring reagents used consisted of an empirically generated hair-binding peptide, a proline spacer, and a carbon black-binding peptide.

The sequences of the triblock peptide-based body surface coloring reagents used in these Examples are given in Table 14. These peptide-based reagents were obtained from Syn-Pep (Dublin, Calif.).

TABLE 14

| | Sequences of Triblock Peptide-Based Body Surface Coloring Reagents | |
| --- | --- | --- |
| Example | Peptide Sequence | SEQ ID NO: |
| 11 | FHENWPS (carbon black-binding peptide) - PPP (spacer) - KKKK (hair-binding peptide) | 138 |
| 12 | FHENWPS (carbon black-binding peptide) - PPP (spacer) - HHHH (hair-binding peptide) | 139 |
| 13 | FHENWPS (carbon black-binding peptide) - PPP (spacer) - RRRR (hair-binding peptide) | 140 |
| 14 | WHLSWSPVPLPT (carbon black-binding peptide) - PPP (spacer) - KKKK (hair-binding peptide) | 141 |
| 15 | WHLSWSPVPLPT (carbon black-binding peptide) - PPP (spacer) - HHHH (hair-binding peptide) | 142 |
| 16 | WHLSWSPVPLPT (carbon black-binding peptide) - PPP (spacer) - RRRR (hair-binding peptide) | 143 |

A 3 wt % solution of the peptide-based body surface coloring reagent to be tested was prepared by dissolving the appropriate amount of the peptide in water. To this aqueous peptide solution was added 1.5 mL of a self-dispersed carbon black pigment dispersion containing 14 wt % solids, prepared as described by Yeh et al. in U.S. Pat. No. 6,852,156, Example 1. The resulting mixture was stirred for 16 h.

A natural white hair swatch, obtained from International Hair Importers, was immersed in the mixture with agitation for 30 min. After this time, the hair swatch was removed from the mixture, allowed to air dry, and then was rinsed with water to remove the unbound pigment. As a control, hair was colored using the same procedure using the carbon black pigment without the peptide reagent. For all the peptide-based body surface coloring reagents tested, the color of the hair was significantly darker black after the water rinse than the control hair sample that was colored without the peptide-based body surface coloring reagent.

Examples 17-20

Biological Production of Triblock Peptide-Based Body Surface Coloring Reagents

The purpose of these Examples was to prepare peptide-based body surface coloring reagents using recombinant DNA and molecular cloning techniques. The peptide-based body surface coloring reagents were triblock structures comprised of hair-binding peptide sequences, and carbon black-binding peptide sequences, separated by peptide spacers. The peptides were expressed in *E. coli* as inclusion bodies. Additional amino acid sequences (i.e., peptide tags) were fused to the peptide-based body surface coloring reagent sequences in order to promote inclusion body formation.

Construction of Production Strains

The sequences of the peptide-based body surface coloring reagents are given in Table 15. DNA sequences were designed to encode these peptides using favorable codons for *E. coli* and avoiding sequence repeats and mRNA secondary structure. The gene DNA sequence was designed by DNA 2.0, Inc. (Menlo Park, Calif.) using proprietary software which is described by Gustafsson et al. (*Trends in Biotechnol.* 22(7):346-355 (2004)). In each case the sequence encoding the amino acid sequence was followed by two termination codons and a recognition site for endonuclease AscI. The GS amino acid sequence at the N-terminus was encoded by a recognition site for endonuclease BamHI (GGA/TCC). The DNA sequences are given by SEQ ID NOs:148-151.

Genes were assembled from synthetic oligonucleotides and cloned into a standard plasmid cloning vector by DNA 2.0, Inc. Sequences were verified by DNA sequencing by DNA 2.0, Inc.

The synthetic genes were excised from the cloning vector with the endonuclease restriction enzymes BamHI and AscI and ligated into an expression vector using standard recombinant DNA methods. The vector pKSIC4-HC77623 was derived from the commercially available vector pDEST17 (Invitrogen, Carlsbad, Calif.). It includes sequences derived from the commercially available vector pET31b (Novagen, Madison, Wis.) that encode a fragment of the enzyme ketosteroid isomerase (KSI). The KSI fragment was included as a fusion partner to promote partition of the peptides into insoluble inclusion bodies in *E. coli*. The KSI-encoding sequence from pET31b was modified using standard mutagenesis procedures (QuickChange II, Stratagene, La Jolla, Calif.) to include three additional Cys codons, in addition to the one Cys codon found in the wild type KSI sequence. The plasmid pKSIC4-HC77623, given by SEQ ID NO:152 and shown in FIG. 1, was constructed using standard recombinant DNA methods, which are well known to those skilled in the art.

The DNA sequences encoding the peptide-based body surface coloring reagents (Table 15) were inserted into pKSIC4-HC77623 by substituting for sequences in the vector between the BamHI and AscI sites. Plasmid DNA containing the peptide encoding sequences and vector DNA were digested with endonuclease restriction enzymes BamHI and AscI, then the peptide-encoding sequences and vector DNA were mixed and ligated by phage T4 DNA ligase using standard DNA cloning procedures, which are well known to those skilled in the art. Correct constructs, in which the sequences encoding the peptide-based body surface coloring reagents were respectively inserted into pKSIC4-HC77623, were identified by restriction analysis and verified by DNA sequencing, using standard methods.

In these constructs, the sequences encoding the peptides of interest were substituted for those encoding HC77623. These sequences were operably linked to the bacteriophage T7 gene 10 promoter and expressed as a fusion protein, fused with the variant KSI partner.

TABLE 15

Sequences of Triblock Peptide-Based Body Surface Coloring Reagents

| Example | Peptide Sequence | Peptide SEQ ID NO: | DNA SEQ ID NO: |
| --- | --- | --- | --- |
| 17 | DPG (spacer) - WHLSWSPVPLPT (carbon black-binding peptide) - GGAGAGG (spacer) - WHLSWSPVPLPT (carbon black-binding peptide) - AGGTSTSKASTTTTSSKTTTTSSKTTTTTSKTSTTSSSSTGGA (spacer) - HEHKNQKETHQRHAA (hair-binding peptide) - GQGGYGGLGSQGAGRGGLGGQG (spacer) - HEHKNQKETHQRHAA (hair-binding peptide) - GGKK (spacer) | 144 | 148 |
| 18 | GSDPG (spacer) - WHLSWSPVPLPT (carbon black-binding peptide) - GGAGGAG (spacer) - WHLSWSPVPLPT (carbon black-binding peptide) - GGTSTSKASTTTTSSKTTTTSSKTTTTTSKTSTTSSSSTGG (spacer) - NTSQLST (hair-binding peptide) - GSGGQGG (spacer) - NTSQLST (hair-binding peptide) - GGPKK (spacer) | 145 | 149 |
| 19 | GSDPG (spacer) - TPPELLHGAPRS (hair-binding peptide) - GGAGGAG (spacer) - WHLSWSPVPLPT (carbon black-binding peptide) - GK (spacer) | 146 | 150 |
| 20 | GSDPG (spacer) - TPPELLHGAPRS (hair-binding peptide) - GGAGGAG (spacer) - TPPELLHGAPRS (hair-binding peptide) - GGAGGAV (spacer) - WHLSWSPVPLPT (carbon black-binding peptide) - GGAGGAG (spacer) - WHLSWSPVPLPT (carbon black-binding peptide) - GK (spacer) | 147 | 151 |

To test the expression of the peptide-based reagents, the expression plasmids were transformed into the BL21-AI *E. coli* strain (Invitrogen, catalog no. C6070-03). To produce the recombinant fusion peptides, 50 mL of LB-ampicillin broth (10 g/L bacto-tryptone, 5 g/L bacto-yeast extract, 10 g/L NaCl, 100 mg/L ampicillin, pH 7.0) was inoculated with the transformed bacteria and the culture was shaken at 37° C. until the $OD_{600}$ reached 0.6. The expression was induced by adding 0.5 mL of 20 wt % L-arabinose to the culture and shaking was continued for another 4 h. Analysis of the cell protein by polyacrylamide gel electrophoresis demonstrated the production of the fusion peptides.

Fermentation:

The recombinant *E. coli* strains, described above, were grown in a 6-L fermentation, which was run in batch mode initially, and then in fed-batch mode. The composition of the fermentation medium is given in Table 16. The pH of the fermentation medium was 6.7. The fermentation medium was sterilized by autoclaving, after which the following sterilized components were added: thiamine hydrochloride (4.5 mg/L), glucose (22.1 g/L), trace elements, see Table 17 (10 mL/L), ampilcillin (100 mg/L), and inoculum (seed) (125 mL). The pH was adjusted as needed using ammonium hydroxide (20 vol %) or phosphoric acid (20 vol %). The added components were sterilized either by autoclaving or filtration.

TABLE 16

Composition of Fermentation Medium

| Component | Concentration |
| --- | --- |
| $KH_2PO_4$ | 9 g/L |
| $(NH_4)_2HPO_4$ | 4 g/L |
| $MgSO_4 \cdot 7H_2O$ | 1.2 g/L |
| Citric Acid | 1.7 g/L |
| Yeast extract | 5.0 g/L |
| Mazu DF 204 Antifoam | 0.1 mL/L |

TABLE 17

Trace Elements

| Component | Concentration, mg/L |
| --- | --- |
| EDTA | 840 |
| $CoCl_2 \cdot H_2O$ | 250 |
| $MnCl_2 \cdot 4H_2O$ | 1500 |
| $CuCl_2 \cdot 2H_2O$ | 150 |
| $H_3BO_3$ | 300 |
| $Na_2MoO_4 \cdot 2H_2O$ | 250 |
| $Zn(CH_3COO)_2 \cdot H_2O$ | 1300 |
| Ferric citrate | 10000 |

The operating conditions for the fermentations are summarized in Table 18. The initial concentration of glucose was 22.1 g/L. When the initial residual glucose was depleted, a pre-scheduled, exponential glucose feed was initiated starting the fed-batch phase of the fermentation run. The glucose feed (see Tables 19 and 20) contained 500 g/L of glucose and was supplemented with 5 g/L of yeast extract. The components of the feed medium were sterilized either by autoclaving or filtration. The goal was to sustain a specific growth rate of 0.13 $h^{-1}$, assuming a yield coefficient (biomass to glucose) of 0.25 g/g, and to maintain the acetic acid levels in the fermentation vessel at very low values (i.e., less than 0.2 g/L). The glucose feed continued until the end of the run. Induction was initiated with a bolus of 2 g/L of L-arabinose at the selected time (i.e., 15 h of elapsed fermentation time). A bolus to deliver 5 g of yeast extract per liter of fermentation broth was added to the fermentation vessel at the following times: 1 h prior to induction, at induction time, and 1 h after induction time. The fermentation run was terminated after 19.97 h of elapsed fermentation time, and 4.97 h after the induction time.

TABLE 18

Fermentation Operating Conditions

| Condition | Initial | Minimum | Maximum |
| --- | --- | --- | --- |
| Stirring | 220 rpm | 220 rpm | 1200 rpm |
| Air Flow | 3 SLPM | 3 SLPM | 30 SLPM |
| Temperature | 37° C. | 37° C. | 37° C. |
| pH | 6.7 | 6.7 | 6.7 |
| Pressure | 0.500 atm (50.7 kPa) | 0.500 atm (50.7 kPa) | 0.500 atm (50.7 kPa) |
| Dissolved $O_2$* | 20% | 20% | 20% |

*Cascade stirrer, then air flow.

TABLE 19

Composition of Feed Medium

| Component | Concentration |
| --- | --- |
| $MgSO_4 \cdot 7H_2O$ | 2.0 g/L |
| Glucose | 500 g/L |
| Ampicillin | 150 mg/L |
| $(NH_4)_2HPO_4$ | 4 g/L |
| $KH_2PO_4$ | 9 g/L |
| Yeast extract | 5.0 g/L |
| Trace Elements - Feed (Table 5) | 10 mL/L |

TABLE 20

Trace Elements - Feed

| Component | Concentration, mg/L |
| --- | --- |
| EDTA | 1300 |
| $CoCl_2 \cdot H_2O$ | 400 |
| $MnCl_2 \cdot 4H_2O$ | 2350 |
| $CuCl_2 \cdot 2H_2O$ | 250 |
| $H_3BO_3$ | 500 |
| $Na_2MoO_4 \cdot 2H_2O$ | 400 |
| $Zn(CH_3COO)_2 \cdot H_2O$ | 1600 |
| Ferric citrate | 4000 |

Isolation and Purification of Peptides:

After completion of the fermentation run, the entire fermentation broth was passed three times through an APV model 2000 Gaulin type homogenizer at 12,000 psi (82,700 kPa). The broth was cooled to below 5° C. prior to each homogenization. The homogenized broth was immediately processed through a Westfalia WhisperFuge™ (Westfalia Separator Inc., Northvale, N.J.) stacked disc centrifuge at 600 mL/min and 12,000 RCF to separate inclusion bodies from suspended cell debris and dissolved impurities. The recovered paste was re-suspended at 15 g/L (dry basis) in water and the pH was adjusted to a value between 8.0 and 10.0 using NaOH. The pH was chosen to help remove cell debris from the inclusion bodies without dissolving the inclusion body proteins. The suspension was passed through the APV 2000 Gaulin type homogenizer at 12,000 psi (82,700 kPa) for a single pass to provide rigorous mixing.

The homogenized high pH suspension was immediately processed in a Westfalia WhisperFuge™ stacked disc centrifuge at 600 mL/min and 12,000 RCF to separate the washed inclusion bodies from suspended cell debris and dissolved impurities. The recovered paste was resuspended at 15 gm/L (dry basis) in pure water. The suspension was passed through the APV 2000 Gaulin type homogenizer at 12,000 psi (82,700 kPa) for a single pass to provide rigorous washing. The homogenized suspension was immediately processed in a Westfalia WhisperFuge™ stacked disc centrifuge at 600 mL/min and 12,000 RCF to separate the washed inclusion bodies from residual suspended cell debris and NaOH.

The recovered paste was resuspended in pure water at 25 g/L (dry basis) and the pH of the mixture was adjusted to 2.2 using HCl. If the peptide being recovered contained cysteine residues, dithiothreitol (DTT, 10 mM) was added to break disulfide bonds. The acidified suspension was heated to 70° C. for 5 to 14 h to complete cleavage of the DP site separating the fusion peptide from the product peptide without damaging the target peptide. The product slurry was adjusted to pH 5.1 (note: the pH used here may vary depending on the solubility of the peptide being recovered) using NaOH and then was cooled to 5° C. and held for 12 h. The mixture was centrifuged at 9000 RCF for 30 min and the supernatant was decanted. The supernatant was then filtered with a 0.2 μm membrane. For some low solubility peptides, multiple washes of the pellet were required to increase peptide recovery.

The filtered product was pH adjusted to 2.0 and mixed with sufficient acetonitrile to yield a solution that was 10 vol % acetonitirile in order to stabilize the samples. This solution was loaded in a 22×250 mm or a 50×250 mm reverse phase chromatography column containing 10 to 15 μm C18 media which was preconditioned with 10 vol % acetonitrile, 90 vol % water with 0.1 vol % trifluoroacetic acid (TFA). The product was recovered in a purified state by eluting the column with a gradient of water and acetonitrile, ramping from 10 vol % to 40 vol % acetonitrile in water with TFA at 0.1 vol %. The eluent containing the product peptide was collected and concentrated by vacuum evaporation by a factor of 2:1 before lyophilization. Spectrophotometric detection at 220 and 278 nm was used to monitor and track elution of the product peptide.

Example 21

Hair Coloring Using a Triblock Peptide-Based Body Surface Coloring Reagent

The purpose of this Example was to demonstrate the coloring of hair using a triblock peptide-based body surface coloring reagent in combination with a carbon black pigment. The color retention was quantified using a spectrophotometic measurement technique.

A self-dispersed carbon black pigment dispersion containing 14 wt % solids, prepared as described by Yeh et al. in U.S. Pat. No. 6,852,156, Example 1, was diluted 1:10 with water. Twenty-five milligrams of the peptide-based body surface coloring reagent given as SEQ ID NO:147, (Example 20) was dissolved in 5 g of water. Then, 10 g of the diluted carbon black pigment dispersion was slowly added to the peptide solution and the solution was mixed for at least 60 min.

A natural white hair swatch, obtained from International Hair Importers, was immersed in the mixture with agitation for 30 min. After this time, the hair swatch was removed from the mixture, allowed to air dry, and then was rinsed with water to remove the unbound pigment. As a control, hair was colored using the same procedure using the carbon black pigment without the peptide reagent.

The color intensity after the water rinse was measured using a X-Rite® SP78™ Sphere Spectrophotometer (X-Rite, Inc., Grandville, Mich.), by placing the colored hair sample into the photosensor and calculating L*, a* and b* parameters representing the photometer response. An initial baseline L* value was measured for the uncolored hair and all measurements were the average of five individual determinations. Delta E values were calculated using equation 1 below:

$$\text{Delta } E = ((L^*_1 - L^*_2)^2 + (a_1 - a_2)^2 + (b_1 - b_2)^2)^{1/2} \quad (1)$$

where L*=the lightness variable and a* and b* are the chromaticity coordinates of CIELAB colorspace as defined by the International Commission of Illumination (CIE) (Minolta, *Precise Color Communication—Color Control From Feeling to Instrumentation*, Minolta Camera Co., 1996). Larger Delta E value are indicative of better color retention. The results are summarized in Table 21.

TABLE 21

Results of Color Retention After Water Rinse

| Sample | Delta E |
|---|---|
| Peptide-based body surface coloring reagent plus pigment | 31.4 |
| Control, pigment alone | 18.2 |

As can be seen from the data in Table 21, the color retention after the water rinse was significantly higher for the sample treated with the peptide-based body surface coloring reagent and the pigment than with the control sample, which was treated with only the pigment.

What is claimed is:

1. A diblock, peptide-based body surface coloring reagent having the general structure $((BSBP)_m\text{-}(PBP)_n)_x$, wherein
   a) BSBP is a body surface binding peptide;
   b) PBP is a pigment-binding peptide; and
   c) m, n, and x independently range from 1 to about 10, and wherein the body surface binding peptide is a hair-binding peptide; and
   wherein either one of or both the body surface binding peptide and the pigment-binding peptide is generated combinatorially by a process selected from the group consisting of phage display, yeast display, bacteria display and combinatorial solid phase peptide synthesis; and
   wherein the surface binding pending peptide is from about 7 to about 50 amino acids.

2. A triblock, peptide-based body surface coloring reagent having the general structure $(((BSBP)_m\text{-}S_q)_x\text{-}((PBP)_n\text{-}S_r)_z)_y$, wherein
   a) BSBP is a body surface binding peptide;
   b) PBP is a pigment-binding peptide;
   c) S is a molecular spacer; and
   d) m, n, x and z independently range from 1 to about 10, y is from 1 to about 5, and
   where q and r are each independently 0 or 1, provided that both r and q may not be 0,
   and wherein the body surface binding peptide is a hair-binding peptide; and
   wherein either one of or both the body surface binding peptide and the pigment-binding peptide is generated combinatorially by a process selected from the group consisting of phage display, yeast display, bacteria display and combinatorial solid phase peptide synthesis; and
   wherein the body surface binding peptide is from about 7 to about 50 amino acids.

3. A peptide-based body surface coloring reagent according to claim 1 or 2 wherein the body surface binding peptide is generated empirically.

4. A peptide-based body surface coloring reagent according to claim 1 or claim 2 wherein the body surface-binding peptide is from about 7 to about 25 amino acids and has a binding affinity for a hair measured as $MB_{50}$, equal to or less than $10^{-5}$ M.

5. A peptide-based body surface coloring reagent according to claim 1 or 2 wherein the pigment-binding peptide is from about 5 to about 50 amino acids.

6. A peptide-based body surface coloring reagent according to claim 1 or 2 wherein the pigment-binding peptide has affinity for a pigment selected from the group consisting of D&C Red No. 36, D&C Red No. 30, D&C Orange No. 17, Green 3 Lake, Ext. Yellow 7 Lake, Orange 4 Lake, Red 28 Lake; the calcium lakes of D&C Red Nos. 7, 11, 31 and 34, the barium lake of D&C Red No. 12, the strontium lake D&C Red No. 13, the aluminum lakes of FD&C Yellow No.5, of FD&C Yellow No. 6, of FD&C No. 40, of D&C Red Nos. 21, 22, 27, and 28, of FD&C Blue No. 1, of D&C Orange No. 5, of D&C Yellow No. 10; the zirconium lake of D&C Red No. 33; iron oxides, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide, titanium dioxide nanoparticles, zinc oxide, barium oxide, ultramarine blue, bismuth citrate, hydroxyapatite, zirconium silicate, and carbon black particles.

7. A triblock peptide-based body surface coloring reagent according to claim 2 wherein the spacer is selected from the group consisting of ethanolamine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl chains, ethyl alkyl chains, propyl alkyl chains, hexyl alkyl chains, steryl alkyl chains, cetyl alkyl chains, and palmitoyl alkyl chains.

8. A triblock peptide-based body surface coloring reagent according to claim 2 wherein the spacer is a peptide comprising from 1 to about 50 amino acids.

9. A triblock peptide-based body surface coloring reagent according to claim 8 wherein the spacer comprises amino acids selected from the group consisting of proline, lysine, glycine, alanine, serine, and mixtures thereof.

10. A peptide-based body surface coloring reagent according to claim 1 or 2 wherein the hair-binding peptide is isolated by a process comprising the steps of:
(i) providing a library of combinatorially generated phage-peptides;
(ii) contacting the library of (i) with hair to form a reaction solution comprising:
(A) phage-peptide-body surface complex;
(B) unbound hair, and
(C) uncomplexed peptides;
(iii) isolating the phage-peptide-hair complex of (ii);
(iv) eluting the weakly bound peptides from the isolated peptide complex of (iii);
(v) identifying the remaining bound phage-peptides either by using polymerase chain reaction directly with the phage-peptide-hair complex remaining after step (iv), or by infecting bacterial host cells directly with the phage-peptide-hair complex remaining after step (iv), growing the infected cells in a suitable growth medium, and isolating and identifying the phage-peptides from the grown cells.

11. A personal care composition comprising an effective amount of the peptide-based body surface coloring reagent of claim 1 or 2.

12. A method for coloring hair comprising:
a) providing a pigment;
b) providing a composition comprising a peptide-based body surface coloring reagent according to claim 1 or 2 wherein the body surface binding peptide has affinity for hair and the pigment binding peptide has affinity for the pigment; and
c) applying the pigment of (a) with the composition of (b) to hair for a time sufficient for the peptide-based body surface coloring reagent to bind to the pigment and the hair.

13. A method according to claim 12 wherein the pigment and the composition comprising a peptide-based body surface coloring reagent are applied to the body surface concomitantly.

14. A method according to claim 12 wherein the pigment is applied to the hair prior to the application of the composition comprising a peptide-based body surface coloring reagent.

15. A method according to claim 12 wherein the composition comprising a peptide based-body surface coloring reagent is applied to the hair prior to the application of the pigment.

16. A method according to claim 12 further comprising the step of:
d) applying a composition comprising a polymeric sealant to the hair subsequent to the applying of the pigment and the composition comprising a peptide-based body surface coloring reagent.

17. A method according to claim 16 wherein the polymeric sealant is selected from the group consisting of poly(allylamine), acrylates, acrylate copolymers, polyurethanes, carbomers, methicones, amodimethicones, polyethylenene glycol, beeswax, and siloxanes.

* * * * *

UNITED STATES PATENT AND TRADEMARK OFFICE
CERTIFICATE OF CORRECTION

PATENT NO. : 7,285,264 B2  
APPLICATION NO. : 11/389948  
DATED : October 23, 2007  
INVENTOR(S) : John P. O'Brien, Hong Wang and Ying Wu Page 1 of 1

It is certified that error appears in the above-identified patent and that said Letters Patent is hereby corrected as shown below:

Column 3, line 25: change "diblock peptide-based body surface coloring having" to --diblock peptide-based body surface coloring reagent having--

Column 3, line 44: change "invention provides aq peptide-" to --invention provides a peptide- --

Column 107, line 57: change "wherein the surface binding pending peptide is" to --wherein the body surface binding peptide is--

Column 109, lines 4-6: change "the calcium lakes of D&C Red Nos. 7, 11, 31 and 34, the barium lake of D&C Red No. 12, the strontium lake of D&C Red No. 13, the aluminum lakes" to --the calcium lakes of D&C Red Nos. 7, 11, 31 and 34; the barium lake of D&C Red No. 12; the strontium lake of D&C Red No. 13; the aluminum lakes--

Signed and Sealed this

Twenty-fourth Day of March, 2009

JOHN DOLL  
*Acting Director of the United States Patent and Trademark Office*

SEQUENCE LISTING

<160> NUMBER OF SEQ ID NOS: 156

<210> SEQ ID NO 1
<211> LENGTH: 8
<212> TYPE: PRT
<213> ORGANISM: Artificial Sequence
<220> FEATURE:
<223> OTHER INFORMATION: Hair-binding peptide

<400> SEQUENCE: 1

Leu Glu Ser Thr Pro Lys Met Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 2

Phe Thr Gln Ser Leu Pro Arg
1               5

<210> SEQ ID NO 3
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 3

Ser Val Ser Val Gly Met Lys Pro Ser Pro Arg Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 4

Leu Asp Val Glu Ser Tyr Lys Gly Thr Ser Met Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Hair-binding peptide.

<400> SEQUENCE: 5

Arg Val Pro Asn Lys Thr Val Thr Val Asp Gly Ala
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 6

Asp Arg His Lys Ser Lys Tyr Ser Ser Thr Lys Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 7

-continued

```
Lys Asn Phe Pro Gln Gln Lys Glu Phe Pro Leu Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 8

Gln Arg Asn Ser Pro Pro Ala Met Ser Arg Arg Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 9

Thr Arg Lys Pro Asn Met Pro His Gly Gln Tyr Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 10

Lys Pro Pro His Leu Ala Lys Leu Pro Phe Thr Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 11

Asn Lys Arg Pro Pro Thr Ser His Arg Ile His Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 12

Asn Leu Pro Arg Tyr Gln Pro Pro Cys Lys Pro Leu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 13

Arg Pro Pro Trp Lys Lys Pro Ile Pro Pro Ser Glu
```

```
                    1               5                   10

<210> SEQ ID NO 14
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 14

Arg Gln Arg Pro Lys Asp His Phe Phe Ser Arg Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Hair-binding peptide
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Glu or Ala

<400> SEQUENCE: 15

Ser Val Pro Asn Lys Xaa Val Thr Val Asp Gly Xaa
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 16

Thr Thr Lys Trp Arg His Arg Ala Pro Val Ser Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 17

Trp Leu Gly Lys Asn Arg Ile Lys Pro Arg Ala Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 18

Ser Asn Phe Lys Thr Pro Leu Pro Leu Thr Gln Ser
1               5                   10

<210> SEQ ID NO 19
<211> LENGTH: 12
<212> TYPE: PRT
```

```
<213> ORGANISM: Artificial Sequence
<220> FEATURE:
<223> OTHER INFORMATION: Hair-binding peptide

<400> SEQUENCE: 19

Lys Glu Leu Gln Thr Arg Asn Val Val Gln Arg Glu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 20

Thr Pro Thr Ala Asn Gln Phe Thr Gln Ser Val Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 21

Ala Ala Gly Leu Ser Gln Lys His Glu Arg Asn Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 22

Glu Thr Val His Gln Thr Pro Leu Ser Asp Arg Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 23

Leu Pro Ala Leu His Ile Gln Arg His Pro Arg Met
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 24

Gln Pro Ser His Ser Gln Ser His Asn Leu Arg Ser
1               5                   10

<210> SEQ ID NO 25
<211> LENGTH: 12
<212> TYPE: PRT
<213> ORGANISM: Artificial Sequence
```

```
<220> FEATURE:
<223> OTHER INFORMATION: Hair-binding peptide

<400> SEQUENCE: 25

Arg Gly Ser Gln Lys Ser Lys Pro Pro Arg Pro Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 26

Thr His Thr Gln Lys Thr Pro Leu Leu Tyr Tyr His
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 27

Thr Lys Gly Ser Ser Gln Ala Ile Leu Lys Ser Thr
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 28

Asp Leu His Thr Val Tyr His
1               5

<210> SEQ ID NO 29
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 29

His Ile Lys Pro Pro Thr Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 30

His Pro Val Trp Pro Ala Ile
1               5

<210> SEQ ID NO 31
<211> LENGTH: 7
<212> TYPE: PRT
<213> ORGANISM: Artificial Sequence
<220> FEATURE:
```

<223> OTHER INFORMATION: Hair-binding peptide

<400> SEQUENCE: 31

Met Pro Leu Tyr Tyr Leu Gln
1               5

<210> SEQ ID NO 32
<211> LENGTH: 26
<212> TYPE: PRT
<213> ORGANISM: Artificial Sequence
<220> FEATURE:
<223> OTHER INFORMATION: Hair-binding peptide

<400> SEQUENCE: 32

His Leu Thr Val Pro Trp Arg Gly Gly Ser Ala Val Pro Phe Tyr
1               5                   10                  15

Ser His Ser Gln Ile Thr Leu Pro Asn His
            20                  25

<210> SEQ ID NO 33
<211> LENGTH: 41
<212> TYPE: PRT
<213> ORGANISM: Artificial Sequence
<220> FEATURE:
<223> OTHER INFORMATION: Hair-binding peptide

<400> SEQUENCE: 33

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
            35                  40

<210> SEQ ID NO 34
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 34

Lys His Pro Thr Tyr Arg Gln
1               5

<210> SEQ ID NO 35
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 35

His Pro Met Ser Ala Pro Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 36

Met Pro Lys Tyr Tyr Leu Gln

```
<210> SEQ ID NO 37
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 37

Met His Ala His Ser Ile Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 38

Thr Ala Ala Thr Thr Ser Pro
1               5

<210> SEQ ID NO 39
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 39

Leu Gly Ile Pro Gln Asn Leu
1               5

<210> SEQ ID NO 40
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 40

Ala Lys Pro Ile Ser Gln His Leu Gln Arg Gly Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 41

Ala Pro Pro Thr Pro Ala Ala Ala Ser Ala Thr Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 42

Asp Pro Thr Glu Gly Ala Arg Arg Thr Ile Met Thr
1               5                   10
```

-continued

```
<210> SEQ ID NO 43
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 43

Glu Gln Ile Ser Gly Ser Leu Val Ala Ala Pro Trp
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 44

Leu Asp Thr Ser Phe Pro Pro Val Pro Phe His Ala
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Hair-binding peptide

<400> SEQUENCE: 45

Leu Pro Arg Ile Ala Asn Thr Trp Ser Pro Ser
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 46

Arg Thr Asn Ala Ala Asp His Pro Ala Ala Val Thr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 47

Ser Leu Asn Trp Val Thr Ile Pro Gly Pro Lys Ile
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 48

Thr Asp Met Gln Ala Pro Thr Lys Ser Tyr Ser Asn
1               5                   10
```

```
<210> SEQ ID NO 49
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 49

Thr Ile Met Thr Lys Ser Pro Ser Leu Ser Cys Gly
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 50

Thr Pro Ala Leu Asp Gly Leu Arg Gln Pro Leu Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 51

Thr Tyr Pro Ala Ser Arg Leu Pro Leu Leu Ala Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 52

Ala Lys Thr His Lys His Pro Ala Pro Ser Tyr Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Hair-binding and nail-binding peptide

<400> SEQUENCE: 53

Tyr Pro Ser Phe Ser Pro Thr Tyr Arg Pro Ala Phe
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 54

Thr Asp Pro Thr Pro Phe Ser Ile Ser Pro Glu Arg
1               5                   10
```

```
<210> SEQ ID NO 55
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 55

Cys Ala Ala Gly Cys Cys Thr Cys Ala Gly Cys Gly Ala Cys Cys Gly
1               5                   10                  15

Ala Ala Thr Ala
            20

<210> SEQ ID NO 56
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 56

Trp His Asp Lys Pro Gln Asn Ser Ser Lys Ser Thr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 57

Asn Glu Val Pro Ala Arg Asn Ala Pro Trp Leu Val
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Hair-binding peptide

<400> SEQUENCE: 58

Asn Ser Pro Gly Tyr Gln Ala Asp Ser Val Ala Ile Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 59

Thr Gln Asp Ser Ala Gln Lys Ser Pro Ser Pro Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Nail-binding peptide

<400> SEQUENCE: 60

Ala Leu Pro Arg Ile Ala Asn Thr Trp Ser Pro Ser
1               5                   10
```

```
<210> SEQ ID NO 61
<211> LENGTH: 12
<212> TYPE: PRT
<213> ORGANISM: Artificial Sequence
<220> FEATURE:
<223> OTHER INFORMATION: Skin-binding peptide

<400> SEQUENCE: 61

Thr Pro Phe His Ser Pro Glu Asn Ala Pro Gly Ser
1               5                   10

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
ccctcatagt tagcgtaacg                                                      20

<210> SEQ ID NO 63
<211> LENGTH: 12
<212> TYPE: PRT
<213> ORGANISM: Artificial Sequence
<220> FEATURE:
<223> OTHER INFORMATION: Control peptide

<400> SEQUENCE: 63

Lys His Gly Pro Asp Leu Leu Arg Ser Ala Pro Arg
1               5                   10

<210> SEQ ID NO 64
<211> LENGTH: 16
<212> TYPE: PRT
<213> ORGANISM: Artificial Sequence
<220> FEATURE:
<223> OTHER INFORMATION: Cysteine-attached hair-binding peptide

<400> SEQUENCE: 64

Arg Thr Asn Ala Ala Asp His Pro Ala Ala Val Thr Gly Gly Gly Cys
1               5                   10                  15

<210> SEQ ID NO 65
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 65

Leu Glu Ser Gly Asp Glu Val Asp
1               5

<210> SEQ ID NO 66
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 66

Thr Pro Pro Glu Leu Leu His Gly Asp Pro Arg Ser
1               5                   10
```

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
caagcctcag cgaccgaata                                                 20

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
cgtaacactg agtttcgtca cca                                             23

<210> SEQ ID NO 69
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 69

Thr Pro Pro Thr Asn Val Leu Met Leu Ala Thr Lys
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 70

Asn Thr Ser Gln Leu Ser Thr
1               5

<210> SEQ ID NO 71
<211> LENGTH: 14
<212> TYPE: PRT
<213> ORGANISM: Artificial Sequence
<220> FEATURE:
<223> OTHER INFORMATION: Biotinylated hair-binding peptide
<220> FEATURE:
<221> NAME/KEY: MISC_FEATURE
<222> LOCATION: (13)..(13)
<223> OTHER INFORMATION: Biotinylated
<220> FEATURE:
<221> NAME/KEY: MISC_FEATURE
<222> LOCATION: (14)..(14)
<223> OTHER INFORMATION: Amidated

<400> SEQUENCE: 71

Arg Thr Asn Ala Ala Asp His Pro Ala Ala Val Thr Lys Cys
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Biotinylated hair-binding peptide
<220> FEATURE:
<221> NAME/KEY: MISC_FEATURE

```
<222> LOCATION: (13)..(13)
<223> OTHER INFORMATION: Biotinylated
<220> FEATURE:
<221> NAME/KEY: MISC_FEATURE
<222> LOCATION: (14)..(14)
<223> OTHER INFORMATION: Amidated

<400> SEQUENCE: 72

Ala Leu Pro Arg Ile Ala Asn Thr Trp Ser Pro Ser Lys Cys
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Biotinylated hair-binding peptide
<220> FEATURE:
<221> NAME/KEY: MISC_FEATURE
<222> LOCATION: (13)..(13)
<223> OTHER INFORMATION: Biotinylated
<220> FEATURE:
<221> NAME/KEY: MISC_FEATURE
<222> LOCATION: (14)..(14)
<223> OTHER INFORMATION: Amidated

<400> SEQUENCE: 73

Thr Pro Pro Glu Leu Leu His Gly Asp Pro Arg Ser Lys Cys
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Biotinylated skin-binding peptide
<220> FEATURE:
<221> NAME/KEY: MISC_FEATURE
<222> LOCATION: (13)..(13)
<223> OTHER INFORMATION: Biotinylated
<220> FEATURE:
<221> NAME/KEY: MISC_FEATURE
<222> LOCATION: (14)..(14)
<223> OTHER INFORMATION: Amidated

<400> SEQUENCE: 74

Thr Pro Phe His Ser Pro Glu Asn Ala Pro Gly Ser Lys Cys
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Hair conditioner resistant hair-binding peptide
<220> FEATURE:
<221> NAME/KEY: MISC_FEATURE
<222> LOCATION: (1)..(1)
<223> OTHER INFORMATION: Fluoroenylmethoxlcarbonyl (Fmoc)-protected
<220> FEATURE:
<221> NAME/KEY: MISC_FEATURE
<222> LOCATION: (1)..(1)
<223> OTHER INFORMATION: 2,2,6,4,7-pentamethyldihydrobenzofuran-
      5sulfonyl-protected
<220> FEATURE:
<221> NAME/KEY: MISC_FEATURE
<222> LOCATION: (2)..(2)
<223> OTHER INFORMATION: t-butyl-protected
<220> FEATURE:
<221> NAME/KEY: MISC_FEATURE
<222> LOCATION: (3)..(3)
<223> OTHER INFORMATION: Trityl-protected
<220> FEATURE:
```

<221> NAME/KEY: MISC_FEATURE
<222> LOCATION: (6)..(6)
<223> OTHER INFORMATION: t-butoxyl-protected
<220> FEATURE:
<221> NAME/KEY: MISC_FEATURE
<222> LOCATION: (7)..(7)
<223> OTHER INFORMATION: Trityl-protected
<220> FEATURE:
<221> NAME/KEY: MISC_FEATURE
<222> LOCATION: (12)..(12)
<223> OTHER INFORMATION: t-butyl-protected

<400> SEQUENCE: 75

Ser Thr Leu His Lys Tyr Lys Ser Gln Asp Pro Thr Pro His His
1               5                   10                  15

<210> SEQ ID NO 76
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 76

Asn Thr Pro Lys Glu Asn Trp
1               5

<210> SEQ ID NO 77
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 77

Asn Thr Pro Ala Ser Asn Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 78

Pro Arg Gly Met Leu Ser Thr
1               5

<210> SEQ ID NO 79
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 79

Pro Pro Thr Tyr Leu Ser Thr
1               5

<210> SEQ ID NO 80
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 80

-continued

```
Thr Ile Pro Thr His Arg Gln His Asp Tyr Arg Ser
1               5                   10
```

<210> SEQ ID NO 81
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 81

```
Thr Pro Pro Thr His Arg Leu
1               5
```

<210> SEQ ID NO 82
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 82

```
Leu Pro Thr Met Ser Thr Pro
1               5
```

<210> SEQ ID NO 83
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 83

```
Leu Gly Thr Asn Ser Thr Pro
1               5
```

<210> SEQ ID NO 84
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 84

```
Thr Pro Leu Thr Gly Ser Thr Asn Leu Leu Ser Ser
1               5                   10
```

<210> SEQ ID NO 85
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 85

```
Thr Pro Leu Thr Lys Glu Thr
1               5
```

<210> SEQ ID NO 86
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 86

```
Gln Gln Ser His Asn Pro Pro
```

```
<210> SEQ ID NO 87
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 87

Thr Gln Pro His Asn Pro Pro
1               5

<210> SEQ ID NO 88
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 88

Ser Thr Asn Leu Leu Arg Thr Ser Thr Val His Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 89

His Thr Gln Pro Ser Tyr Ser Ser Thr Asn Leu Phe
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 90

Ser Leu Leu Ser Ser His Ala
1               5

<210> SEQ ID NO 91
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 91

Gln Gln Ser Ser Ile Ser Leu Ser Ser His Ala Val
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 92

Asn Ala Ser Pro Ser Ser Leu
1               5
```

```
<210> SEQ ID NO 93
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 93

His Ser Pro Ser Ser Leu Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Hair-binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 94

Lys Xaa Ser His His Thr His
1               5

<210> SEQ ID NO 95
<211> LENGTH: 7
<212> TYPE: PRT
<213> ORGANISM: Artificial Sequence
<220> FEATURE:
<223> OTHER INFORMATION: Hair-binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 95

Glu Xaa Ser His His Thr His
1               5

<210> SEQ ID NO 96
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 96

Leu Glu Ser Thr Ser Leu Leu
1               5

<210> SEQ ID NO 97
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 97

Thr Pro Leu Thr Lys Glu Thr
1               5

<210> SEQ ID NO 98
<211> LENGTH: 7
<212> TYPE: PRT
<213> ORGANISM: Artificial Sequence
```

```
<220> FEATURE:
<223> OTHER INFORMATION: Hair-binding peptide

<400> SEQUENCE: 98

Lys Gln Ser His Asn Pro Pro
1               5

<210> SEQ ID NO 99
<211> LENGTH: 12
<212> TYPE: PRT
<213> ORGANISM: Artificial Sequence
<220> FEATURE:
<223> OTHER INFORMATION: Skin-binding sequence

<400> SEQUENCE: 99

Lys Gln Ala Thr Phe Pro Pro Asn Pro Thr Ala Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Skin-binding peptide

<400> SEQUENCE: 100

His Gly His Met Val Ser Thr Ser Gln Leu Ser Ile
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 101

Leu Ser Pro Ser Arg Met Lys
1               5

<210> SEQ ID NO 102
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 102

Leu Pro Ile Pro Arg Met Lys
1               5

<210> SEQ ID NO 103
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 103

His Gln Arg Pro Tyr Leu Thr
1               5

<210> SEQ ID NO 104
<211> LENGTH: 7
<212> TYPE: PRT
<213> ORGANISM: Artificial Sequence
<220> FEATURE:
```

<223> OTHER INFORMATION: Skin-binding peptide

<400> SEQUENCE: 104

Phe Pro Pro Leu Leu Arg Leu
1               5

<210> SEQ ID NO 105
<211> LENGTH: 12
<212> TYPE: PRT
<213> ORGANISM: Artificial Sequence
<220> FEATURE:
<223> OTHER INFORMATION: Empirically generated hair and skin-binding
      peptide

<400> SEQUENCE: 105

Lys Arg Gly Arg His Lys Arg Pro Lys Arg His Lys
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Empirically generated hair and skin-binding
      peptide

<400> SEQUENCE: 106

Arg Leu Leu Arg Leu Leu Arg
1               5

<210> SEQ ID NO 107
<211> LENGTH: 12
<212> TYPE: PRT
<213> ORGANISM: Artificial Sequence
<220> FEATURE:
<223> OTHER INFORMATION: Empirically generated hair and skin-binding
      peptide

<400> SEQUENCE: 107

His Lys Pro Arg Gly Gly Arg Lys Lys Ala Leu His
1               5                   10

<210> SEQ ID NO 108
<211> LENGTH: 18
<212> TYPE: PRT
<213> ORGANISM: Artificial Sequence
<220> FEATURE:
<223> OTHER INFORMATION: Empirically generated hair and skin-binding
      peptide

<400> SEQUENCE: 108

Lys Pro Arg Pro Pro His Gly Lys Lys His Arg Pro Lys His Arg Pro
1               5                   10                  15

Lys Lys

<210> SEQ ID NO 109
<211> LENGTH: 18
<212> TYPE: PRT
<213> ORGANISM: Artificial Sequence
<220> FEATURE:
<223> OTHER INFORMATION: Empirically generated hair and skin-binding
      peptide

<400> SEQUENCE: 109

Arg Gly Arg Pro Lys Lys Gly His Gly Lys Arg Pro Gly His Arg Ala
1               5                   10                  15

Arg Lys

<210> SEQ ID NO 110
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 110

Met Pro Pro Pro Leu Met Gln
1               5

<210> SEQ ID NO 111
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 111

Phe His Glu Asn Trp Pro Ser
1               5

<210> SEQ ID NO 112
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 112

Arg Thr Ala Pro Thr Thr Pro Leu Leu Leu Ser Leu
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 113

Trp His Leu Ser Trp Ser Pro Val Pro Leu Pro Thr
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 114

Pro His Ala Arg Leu Val Gly
1               5

<210> SEQ ID NO 115
<211> LENGTH: 14
<212> TYPE: PRT
<213> ORGANISM: Artificial Sequence
<220> FEATURE:
<223> OTHER INFORMATION: Pigment-binding peptide

<400> SEQUENCE: 115

Asn Ile Pro Tyr His His Pro Asn Ile Pro Tyr His His Pro
1               5                   10

```
<210> SEQ ID NO 116
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 116

Thr Thr Met Pro Ala Ile Pro
1               5

<210> SEQ ID NO 117
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 117

His Asn Leu Pro Pro Arg Ser
1               5

<210> SEQ ID NO 118
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 118

Ala His Lys Thr Gln Met Gly Val Arg Gln Pro Ala
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 119

Ala Asp Asn Val Gln Met Gly Val Ser His Thr Pro
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 120

Ala His Asn Ala Gln Met Gly Val Ser His Pro Pro
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 121

Ala Asp Tyr Val Gly Met Gly Val Ser His Arg Pro
1               5                   10
```

```
<210> SEQ ID NO 122
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 122

Ser Val Ser Val Gly Met Lys Pro Ser Pro Arg Pro
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 123

Tyr Pro Asn Thr Ala Leu Val
1               5

<210> SEQ ID NO 124
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 124

Val Ala Thr Arg Ile Val Ser
1               5

<210> SEQ ID NO 125
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 125

His Ser Leu Lys Asn Ser Met Leu Thr Val Met Ala
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 126

Asn Tyr Pro Thr Gln Ala Pro
1               5

<210> SEQ ID NO 127
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 127

Lys Cys Cys Tyr Ser Val Gly
1               5
```

```
<210> SEQ ID NO 128
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 128

Arg His Asp Leu Asn Thr Trp Leu Pro Pro Val Lys
1               5                   10

<210> SEQ ID NO 129
<211> LENGTH: 12
<212> TYPE: PRT
<213> ORGANISM: Pigment-binding peptide

<400> SEQUENCE: 129

Glu Ile Ser Leu Pro Ala Lys Leu Pro Ser Ala Ser
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 130

Tyr Val Cys Glu Gly Ile His Pro Cys Pro Arg Pro
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 131

Ser Asp Tyr Val Gly Met Arg Pro Ser Pro Arg His
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 132

Ser Asp Tyr Val Gly Met Arg Leu Ser Pro Ser Gln
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 133

Ser Val Ser Val Gly Ile Gln Pro Ser Pro Arg Pro
1               5                   10

<210> SEQ ID NO 134
<211> LENGTH: 12
<212> TYPE: PRT
```

<213> ORGANISM: Artificial Sequence
<220> FEATURE:
<223> OTHER INFORMATION: Pigment-binding peptide

<400> SEQUENCE: 134

Tyr Val Ser Val Gly Ile Lys Pro Ser Pro Arg Pro
1               5                   10

<210> SEQ ID NO 135
<211> LENGTH: 37
<212> TYPE: PRT
<213> ORGANISM: Artificial Sequence
<220> FEATURE:
<223> OTHER INFORMATION: Peptide spacer

<400> SEQUENCE: 135

Thr Ser Thr Ser Lys Ala Ser Thr Thr Thr Ser Ser Lys Thr Thr
1               5                   10                  15

Thr Thr Ser Ser Lys Thr Thr Thr Thr Ser Lys Thr Ser Thr Thr
            20                  25                  30

Ser Ser Ser Ser Thr
        35

<210> SEQ ID NO 136
<211> LENGTH: 22
<212> TYPE: PRT
<213> ORGANISM: Artificial Sequence
<220> FEATURE:
<223> OTHER INFORMATION: Peptide spacer

<400> SEQUENCE: 136

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 137
<211> LENGTH: 10
<212> TYPE: PRT
<213> ORGANISM: Artificial Sequence
<220> FEATURE:
<223> OTHER INFORMATION: Peptide spacer

<400> SEQUENCE: 137

Gly Pro Gly Gly Tyr Gly Pro Gly Gln Gln
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Triblock peptide-based body surface reagent

<400> SEQUENCE: 138

Phe His Glu Asn Trp Pro Ser Pro Pro Pro Lys Lys Lys Lys
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Triblock peptide-based body surface reagent

<400> SEQUENCE: 139

```
Phe His Glu Asn Trp Pro Ser Pro Pro His His His
1               5                  10
```

<210> SEQ ID NO 140
<211> LENGTH: 14
<212> TYPE: PRT
<213> ORGANISM: Artificial Sequence
<220> FEATURE:
<223> OTHER INFORMATION: Triblock peptide-based body surface reagent

<400> SEQUENCE: 140

```
Phe His Glu Asn Trp Pro Ser Pro Pro Arg Arg Arg Arg
1               5                  10
```

<210> SEQ ID NO 141
<211> LENGTH: 19
<212> TYPE: PRT
<213> ORGANISM: Artificial Sequence
<220> FEATURE:
<223> OTHER INFORMATION: Triblock peptide-based body surface reagent

<400> SEQUENCE: 141

```
Trp His Leu Ser Trp Ser Pro Val Pro Leu Pro Thr Pro Pro Lys
1               5                  10                  15

Lys Lys Lys
```

<210> SEQ ID NO 142
<211> LENGTH: 19
<212> TYPE: PRT
<213> ORGANISM: Artificial Sequence
<220> FEATURE:
<223> OTHER INFORMATION: Triblock peptide-based body surface reagent

<400> SEQUENCE: 142

```
Trp His Leu Ser Trp Ser Pro Val Pro Leu Pro Thr Pro Pro His
1               5                  10                  15

His His His
```

<210> SEQ ID NO 143
<211> LENGTH: 19
<212> TYPE: PRT
<213> ORGANISM: Artificial Sequence
<220> FEATURE:
<223> OTHER INFORMATION: Triblock peptide-based body surface reagent

<400> SEQUENCE: 143

```
Trp His Leu Ser Trp Ser Pro Val Pro Leu Pro Thr Pro Pro Arg
1               5                  10                  15

Arg Arg Arg
```

<210> SEQ ID NO 144
<211> LENGTH: 133
<212> TYPE: PRT
<213> ORGANISM: Artificial Sequence
<220> FEATURE:
<223> OTHER INFORMATION: Multicopy peptide-based body surface coloring
      reagent

<400> SEQUENCE: 144

```
Asp Pro Gly Trp His Leu Ser Trp Ser Pro Val Pro Leu Pro Thr Gly
1               5                  10                  15

Gly Ala Gly Ala Gly Gly Trp His Leu Ser Trp Ser Pro Val Pro Leu
            20                  25                  30
```

```
Pro Thr Ala Gly Gly Thr Ser Thr Ser Lys Ala Ser Thr Thr Thr Thr
            35                  40                  45

Ser Ser Lys Thr Thr Thr Thr Ser Ser Lys Thr Thr Thr Thr Thr Ser
    50                  55                  60

Lys Thr Ser Thr Thr Ser Ser Ser Thr Gly Gly Ala His Glu His
 65                  70                  75                  80

Lys Asn Gln Lys Glu Thr His Gln Arg His Ala Ala Gly Gln Gly Gly
                85                  90                  95

Tyr Gly Gly Leu Gly Ser Gln Gly Ala Gly Arg Gly Gly Leu Gly Gly
            100                 105                 110

Gln Gly His Glu His Lys Asn Gln Lys Glu Thr His Gln Arg His Ala
            115                 120                 125

Ala Gly Gly Lys Lys
        130

<210> SEQ ID NO 145
<211> LENGTH: 103
<212> TYPE: PRT
<213> ORGANISM: Artificial Sequence
<220> FEATURE:
<223> OTHER INFORMATION: Multicopy peptide-based body surface coloring
      reagent

<400> SEQUENCE: 145

Gly Ser Asp Pro Gly Trp His Leu Ser Trp Ser Pro Val Pro Leu Pro
 1               5                  10                  15

Thr Gly Gly Ala Gly Gly Ala Gly Trp His Leu Ser Trp Ser Pro Val
            20                  25                  30

Pro Leu Pro Thr Gly Gly Thr Ser Thr Ser Lys Ala Ser Thr Thr Thr
            35                  40                  45

Thr Ser Ser Lys Thr Thr Thr Thr Ser Ser Lys Thr Thr Thr Thr Thr
    50                  55                  60

Ser Lys Thr Ser Thr Thr Ser Ser Ser Thr Gly Gly Asn Thr Ser
 65                  70                  75                  80

Gln Leu Ser Thr Gly Ser Gly Gln Gly Gly Asn Thr Ser Gln Leu
                85                  90                  95

Ser Thr Gly Gly Pro Lys Lys
            100

<210> SEQ ID NO 146
<211> LENGTH: 38
<212> TYPE: PRT
<213> ORGANISM: Artificial Sequence
<220> FEATURE:
<223> OTHER INFORMATION: Peptide-based body surface coloring reagent

<400> SEQUENCE: 146

Gly Ser Asp Pro Gly Thr Pro Pro Glu Leu Leu His Gly Ala Pro Arg
 1               5                  10                  15

Ser Gly Gly Ala Gly Gly Ala Gly Trp His Leu Ser Trp Ser Pro Val
            20                  25                  30

Pro Leu Pro Thr Gly Lys
        35

<210> SEQ ID NO 147
<211> LENGTH: 76
<212> TYPE: PRT
<213> ORGANISM: Artificial Sequence
<220> FEATURE:
<223> OTHER INFORMATION: Multicopy peptide-based body surface coloring
```

-continued reagent

<400> SEQUENCE: 147

Gly Ser Asp Pro Gly Thr Pro Pro Glu Leu Leu His Gly Ala Pro Arg
1               5                   10                  15

Ser Gly Gly Ala Gly Gly Ala Gly Thr Pro Pro Glu Leu Leu His Gly
            20                  25                  30

Ala Pro Arg Ser Gly Gly Ala Gly Gly Ala Val Trp His Leu Ser Trp
        35                  40                  45

Ser Pro Val Pro Leu Pro Thr Gly Gly Ala Gly Ala Gly Trp His
    50                  55                  60

Leu Ser Trp Ser Pro Val Pro Leu Pro Thr Gly Lys
65                  70                  75

<210> SEQ ID NO 148
<211> LENGTH: 419
<212> TYPE: DNA
<213> ORGANISM: Artificial Sequence
<220> FEATURE:
<223> OTHER INFORMATION: Coding sequence for peptide-based body surface
      coloring reagent

<400> SEQUENCE: 148
ggatccgacc ctggttggca cctgtcttgg tccctgttc ctctgccgac cggtggtgca      60
ggcgctggtg gctggcacct gtcctggagc cctgtcccgc tgccgactgc ggcggtact    120 tctacctcca aagcgtccac gaccactacc agcagcaaaa ccacgaccac cagctctaaa   180
actaccacta ccaccagcaa gacctccact accagctctt cttctactgg tggcgcccat   240
gaacataaaa accagaaaga aacccaccag cgtcacgctg cgggtcaagg cggttacggt   300
ggcctgggta gccagggtgc aggtcgcggt ggtctgggtg gccagggtca cgaacacaag   360
aatcagaaag aaacgcacca gcgccacgct gcgggtggca aaaagtaata aggcgcgcc    419

<210> SEQ ID NO 149
<211> LENGTH: 323
<212> TYPE: DNA
<213> ORGANISM: Artificial Sequence
<220> FEATURE:
<223> OTHER INFORMATION: Coding sequence for peptide-based body surface
      coloring reagent

<400> SEQUENCE: 149
ggatccgacc ctggctggca tctgtcttgg agccctgtac ctctgccgac tggcggcgca      60
ggcggtgcag gttggcacct gagctggtcc ccagtaccgc tgccgacggg cggcaccagc   120
acttctaaag caagcaccac cactaccagc tccaagacca ctaccacttc ttccaaaacc    180
accacgacca cttctaagac ttctactact tctagcagct ctaccggtgg taatacttct    240
cagctgagca ccggcagcgg cggtcagggt ggcaatacgt ctcagctgtc caccggtggc   300
ccgaaaaagt aataaggcgc gcc                                            323

<210> SEQ ID NO 150
<211> LENGTH: 323
<212> TYPE: DNA
<213> ORGANISM: Artificial Sequence
<220> FEATURE:
<223> OTHER INFORMATION: Coding sequence for peptide-based body surface
      coloring reagent

<400> SEQUENCE: 150
ggatccgacc ctggctggca tctgtcttgg agccctgtac ctctgccgac tggcggcgca      60

-continued

```
ggcggtgcag gttggcacct gagctggtcc ccagtaccgc tgccgacggg cggcaccagc    120
acttctaaag caagcaccac cactaccagc tccaagacca ctaccacttc ttccaaaacc    180
accacgacca cttctaagac ttctactact tctagcagct ctaccggtgg taatacttct    240
cagctgagca ccggcagcgg cggtcagggt ggcaatacgt ctcagctgtc caccggtggc    300
ccgaaaaagt aataaggcgc gcc                                            323
```

<210> SEQ ID NO 151
<211> LENGTH: 242
<212> TYPE: DNA
<213> ORGANISM: Artificial Sequence
<220> FEATURE:
<223> OTHER INFORMATION: Coding sequence for peptide-based body surface coloring reagent

<400> SEQUENCE: 151

```
ggatccgacc caggtactcc tccagaactg ctgcatggtg ctccacgttc tggcggtgct     60
ggtggtgccg gcacccctcc agaactgctg cacggcgcac cgcgctctgg cggtgcaggt    120
ggcgcagttt ggcacctgtc ctggtcccct gtgccgctgc caaccggtgg cgcggtggt    180 gctggttggc acctgagctg gagcccggtt cctctgccga ccggtaaatg atgaggcgcg    240
cc                                                                   242
```

<210> SEQ ID NO 152
<211> LENGTH: 5388
<212> TYPE: DNA
<213> ORGANISM: Artificial Sequence
<220> FEATURE:
<223> OTHER INFORMATION: Plasmid pKSIC4-HCC77623

<400> SEQUENCE: 152

```
agatctcgat cccgcgaaat taatacgact cactataggg agaccacaac ggtttccctc     60
tagaaataat tttgtttaac tttaagaagg agatatacat atgcataccc agaacacat    120 caccgccgtg gtacagcgct tgtggctgc gctcaatgcc ggcgatctgg acggcatcgt    180
cgcgctgttt gccgatgacg ccacggtgga agagcccgtg ggttccgagc caggtccgg    240 tacggctgcg tgtcgtgagt tttacgccaa ctcgctcaaa ctgcctttgg cggtggagct    300
gacgcaggag tgccgcgcgg tcgccaacga agcggccttc gctttcaccg tcagcttcga    360
gtatcagggc cgcaagaccg tagttgcgcc ctgtgatcac tttcgcttca atggcgccgg    420
caaggtggtg agcatccgcg ccttgttttgg cgagaagaat attcacgcat gccagggatc    480
cgatccgact ccgccgacga atgtactgat gctggcaacc aaaggcggtg gtacgcattc    540
cacgcacaac catggcagcc cgcgccacac gaatgctgac gcaggcaatc cgggcggcgg    600 cacccccacca accaatgtcc tgatgctggc tactaaaggc ggcggcacgc attctaccca    660
caaccatggt agcccgcgcc atactaatgc agatgccgga aacccgggcg gtggtacccc    720
gccaaccaac gttctgatgc tggcgacgaa aggtggcggt acccattcca cgcataatca    780
tggcagccct cgccacacca cgctgatgc tggtaatcct ggtggcggta agaagaaata    840
ataaggcgcg ccgacccagc tttcttgtac aaagtggttg attcgaggct gctaacaaag    900
cccgaaagga agctgagttg gctgctgcca ccgctgagca ataactagca taaccccttg    960
gggcctctaa acgggtcttg aggggttttt tgctgaaagg aggaactata tccggatatc   1020
cacaggacgg gtgtggtcgc catgatcgcg tagtcgatag tggctccaag tagcgaagcg   1080
agcaggactg ggcggcggcc aaagcggtcg gacagtgctc cgagaacggg tgcgcataga   1140
```

-continued

```
aattgcatca acgcatatag cgctagcagc acgccatagt gactggcgat gctgtcggaa    1200
tggacgatat cccgcaagag gcccggcagt accggcataa ccaagcctat gcctacagca    1260
tccagggtga cggtgccgag gatgacgatg agcgcattgt tagatttcat acacggtgcc    1320
tgactgcgtt agcaatttaa ctgtgataaa ctaccgcatt aaagcttatc gatgataagc    1380
tgtcaaacat gagaattctt gaagacgaaa gggcctcgtg atacgcctat ttttataggt    1440
taatgtcatg ataataatgg tttcttagac gtcaggtggc acttttcggg gaaatgtgcg    1500
cggaacccct atttgtttat ttttctaaat acattcaaat atgtatccgc tcatgagaca    1560
ataaccctga taaatgcttc aataatattg aaaaggaag agtatgagta ttcaacattt     1620
ccgtgtcgcc cttattccct tttttgcggc attttgcctt cctgtttttg ctcacccaga    1680
aacgctggtg aaagtaaaag atgctgaaga tcagttgggt gcacgagtgg gttacatcga    1740
actggatctc aacagcggta agatccttga gagttttcgc cccgaagaac gttttccaat    1800
gatgagcact tttaaagttc tgctatgtgg cgcggtatta tcccgtgttg acgccgggca    1860
agagcaactc ggtcgccgca tacactattc tcagaatgac ttggttgagt actcaccagt    1920
cacagaaaag catcttacgg atggcatgac agtaagagaa ttatgcagtg ctgccataac    1980
catgagtgat aacactgcgg ccaacttact tctgacaacg atcggaggac cgaaggagct    2040
aaccgctttt ttgcacaaca tgggggatca tgtaactcgc cttgatcgtt gggaaccgga    2100
gctgaatgaa gccataccaa acgacgagcg tgacaccacg atgcctgcag caatggcaac    2160
aacgttgcgc aaactattaa ctggcgaact acttactcta gcttcccggc aacaattaat    2220
agactggatg gaggcggata aagttgcagg accacttctg cgctcggccc ttccggctgg    2280
ctggtttatt gctgataaat ctggagccgg tgagcgtggg tctcgcggta tcattgcagc    2340
actggggcca gatggtaagc cctcccgtat cgtagttatc tacacgacgg ggagtcaggc    2400
aactatggat gaacgaaata gacagatcgc tgagataggt gcctcactga ttaagcattg    2460
gtaactgtca gaccaagttt actcatatat actttagatt gatttaaaac ttcattttta    2520
atttaaaagg atctaggtga agatcctttt tgataatctc atgaccaaaa tcccttaacg    2580
tgagttttcg ttccactgag cgtcagaccc cgtagaaaag atcaaaggat cttcttgaga    2640 tcctttttt ctgcgcgtaa tctgctgctt gcaaacaaaa aaaccaccgc taccagcggt     2700
ggtttgtttg ccggatcaag agctaccaac tctttttccg aaggtaactg gcttcagcag    2760
agcgcagata ccaaatactg tccttctagt gtagccgtag ttaggccacc acttcaagaa    2820
ctctgtagca ccgcctacat acctcgctct gctaatcctg ttaccagtgg ctgctgccag    2880
tggcgataag tcgtgtctta ccgggttgga ctcaagacga tagttaccgg ataaggcgca    2940
gcggtcgggc tgaacggggg gttcgtgcac acagcccagc ttggagcgaa cgacctacac    3000
cgaactgaga tacctacagc gtgagctatg agaaagcgcc acgcttcccg aagggagaaa    3060
ggcggacagg tatccggtaa gcggcagggt cggaacagga gagcgcacga gggagcttcc    3120
agggggaaac gcctggtatc tttatagtcc tgtcgggttt cgccacctct gacttgagcg    3180
tcgatttttg tgatgctcgt cagggggcg gagcctatgg aaaaacgcca gcaacgcggc     3240 cttttacgg ttcctggcct tttgctggcc ttttgctcac atgttctttc ctgcgttatc     3300
ccctgattct gtggataacc gtattaccgc ctttgagtga gctgataccg ctcgccgcag    3360
ccgaacgacc gagcgcagcg agtcagtgag cgaggaagcg gaagagcgcc tgatgcggta    3420
ttttctcctt acgcatctgt gcggtatttc acaccgcata tatggtgcac tctcagtaca    3480
```

```
atctgctctg atgccgcata gttaagccag tatacactcc gctatcgcta cgtgactggg    3540
tcatggctgc gccccgacac ccgccaacac ccgctgacgc ccctgacgg gcttgtctgc    3600 tcccggcatc cgcttacaga caagctgtga ccgtctccgg gagctgcatg tgtcagaggt    3660
tttcaccgtc atcaccgaaa cgcgcgaggc agctgcggta aagctcatca gcgtggtcgt    3720
gaagcgattc acagatgtct gcctgttcat ccgcgtccag ctcgttgagt ttctccagaa    3780
gcgttaatgt ctggcttctg ataaagcggg ccatgttaag gcggttttt tcctgtttgg     3840 tcactgatgc ctccgtgtaa gggggatttc tgttcatggg ggtaatgata ccgatgaaac    3900
gagagaggat gctcacgata cgggttactg atgatgaaca tgcccggtta ctggaacgtt    3960
gtgagggtaa acaactggcg gtatggatgc ggcgggacca gagaaaaatc actcagggtc    4020
aatgccagcg cttcgttaat acagatgtag gtgttccaca gggtagccag cagcatcctg    4080
cgatgcagat ccggaacata atggtgcagg cgctgactt ccgcgtttcc agactttacg     4140
aaacacggaa accgaagacc attcatgttg ttgctcaggt cgcagacgtt ttgcagcagc    4200
agtcgcttca cgttcgctcg cgtatcggtg attcattctg ctaaccagta aggcaacccc    4260
gccagcctag ccgggtcctc aacgacagga gcacgatcat cgcacccgt ggccaggacc     4320 caacgctgcc cgagatgcgc cgcgtgcggc tgctggagat ggcggacgcg atggatatgt    4380
tctgccaagg gttggtttgc gcattcacag ttctccgcaa gaattgattg ctccaattc     4440 ttggagtggt gaatccgtta gcgaggtgcc gccggcttcc attcaggtcg aggtggcccg    4500
gctccatgca ccgcgacgca acgcggggag gcagacaagg tatagggcgg cgcctacaat    4560
ccatgccaac ccgttccatg tgctcgccga ggcggcataa atcgccgtga cgatcagcgg    4620
tccagtgatc gaagttaggc tggtaagagc cgcgagcgat ccttgaagct gtccctgatg    4680
gtcgtcatct acctgcctgg acagcatggc ctgcaacgcg ggcatcccga tgccgccgga    4740
agcgagaaga atcataatgg ggaaggccat ccagcctcgc gtcgcgaacg ccagcaagac    4800
gtagcccagc gcgtcggccg ccatgccggc gataatggcc tgcttctcgc cgaaacgttt    4860
ggtggcggga ccagtgacga aggcttgagc gagggcgtgc aagattccga ataccgcaag    4920
cgacaggccg atcatcgtcg cgctccagcg aaagcggtcc tcgccgaaaa tgacccagag    4980
cgctgccggc acctgtccta cgagttgcat gataaagaag acagtcataa gtgcggcgac    5040
gatagtcatg ccccgcgccc accggaagga gctgactggg ttgaaggctc tcaagggcat    5100
cggtcgatcg acgctctccc ttatgcgact cctgcattag gaagcagccc agtagtaggt    5160
tgaggccgtt gagcaccgcc gccgcaagga atggtgcatg caaggagatg cgcccaaca    5220 gtccccggc cacggggcct gccaccatac ccacgccgaa acaagcgctc atgagcccga     5280
agtggcgagc ccgatcttcc ccatcggtga tgtcggcgat ataggcgcca gcaaccgcac    5340
ctgtggcgcc ggtgatgccg gccacgatgc gtccggcgta gaggatcg                5388
```

<210> SEQ ID NO 153
<211> LENGTH: 12
<212> TYPE: PRT
<213> ORGANISM: Artificial Sequence
<220> FEATURE:
<223> OTHER INFORMATION: Hair conditioner and shampoo resistant
      hair-binding peptide

<400> SEQUENCE: 153

Gly Met Pro Ala Met His Trp Ile His Pro Phe Ala
1               5                   10

```
<210> SEQ ID NO 154
<211> LENGTH: 15
<212> TYPE: PRT
<213> ORGANISM: Artificial Sequence
<220> FEATURE:
<223> OTHER INFORMATION: Hair conditioner and shampoo resistant
      hair-binding peptide

<400> SEQUENCE: 154

His Asp His Lys Asn Gln Lys Glu Thr His Gln Arg His Ala Ala
1               5                   10                  15

<210> SEQ ID NO 155
<211> LENGTH: 20
<212> TYPE: PRT
<213> ORGANISM: Artificial Sequence
<220> FEATURE:
<223> OTHER INFORMATION: Hair conditioner and shampoo resistant
      hair-binding peptide

<400> SEQUENCE: 155

His Asn His Met Gln Glu Arg Tyr Thr Asp Pro Gln His Ser Pro Ser
1               5                   10                  15

Val Asn Gly Leu
            20

<210> SEQ ID NO 156
<211> LENGTH: 20
<212> TYPE: PRT
<213> ORGANISM: Artificial Sequence
<220> FEATURE:
<223> OTHER INFORMATION: Hair conditioner and shampoo resistant
      hair-binding peptide

<400> SEQUENCE: 156

Thr Ala Glu Ile Gln Ser Ser Lys Asn Pro Asn Pro His Pro Gln Arg
1               5                   10                  15

Ser Trp Thr Asn
            20
```